(12) United States Patent
Haran

(10) Patent No.: US 11,739,373 B2
(45) Date of Patent: Aug. 29, 2023

(54) SYSTEMS AND METHODS FOR MULTIPLEXED ANALYTE DETECTION USING ANTIBODY-OLIGONUCLEOTIDE CONJUGATES

(71) Applicant: G1 Sciences, LLC, Wilmington, DE (US)

(72) Inventor: Sudha Haran, Lawrence Township, NJ (US)

(73) Assignee: G1 Sciences, LLC, Wilmington, DE (US)

( * ) Notice: Subject to any disclaimer, the term of this patent is extended or adjusted under 35 U.S.C. 154(b) by 413 days.

(21) Appl. No.: 16/268,321

(22) Filed: Feb. 5, 2019

(65) Prior Publication Data
US 2019/0241939 A1   Aug. 8, 2019

Related U.S. Application Data

(60) Provisional application No. 62/641,191, filed on Mar. 9, 2018, provisional application No. 62/626,637, filed on Feb. 5, 2018.

(51) Int. Cl.
| | |
|---|---|
| *C12Q 1/68* | (2018.01) |
| *C12Q 1/6837* | (2018.01) |
| *C12Q 1/00* | (2006.01) |
| *C12Q 1/6853* | (2018.01) |
| *C12Q 1/6851* | (2018.01) |
| *C12Q 1/6874* | (2018.01) |
| *C12Q 1/686* | (2018.01) |
| *G01N 33/543* | (2006.01) |
| *C12Q 1/6804* | (2018.01) |

(52) U.S. Cl.
CPC .......... *C12Q 1/6837* (2013.01); *C12Q 1/005* (2013.01); *C12Q 1/6804* (2013.01); *C12Q 1/686* (2013.01); *C12Q 1/6851* (2013.01); *C12Q 1/6853* (2013.01); *C12Q 1/6874* (2013.01); *G01N 33/54306* (2013.01); *C12Q 2565/537* (2013.01); *G01N 2458/10* (2013.01)

(58) Field of Classification Search
CPC ........................................................ C12Q 1/68
USPC ........................................................ 435/6.1
See application file for complete search history.

(56) References Cited

U.S. PATENT DOCUMENTS

| | | | | |
|---|---|---|---|---|
| 2012/0316086 | A1* | 12/2012 | Lin ...................... | C12Q 1/6837 506/26 |
| 2013/0059741 | A1* | 3/2013 | Weiner ................. | C12Q 1/6804 506/4 |
| 2013/0274115 | A1* | 10/2013 | Rigatti ................. | C12Q 1/6874 506/2 |

(Continued)

FOREIGN PATENT DOCUMENTS

WO   WO-2013088935 A1 *   6/2013   ........... C12Q 1/6844

OTHER PUBLICATIONS

Skerra (Phosphorothioate primers improve the amplification of DNA sequences by DNA polymerases with proofreading activity, Nucleic Acids Res. Jul. 25, 1992; 20(14): 3551-3554).*

(Continued)

*Primary Examiner* — Aaron A Priest
(74) *Attorney, Agent, or Firm* — Wolf, Greenfield & Sacks, P.C.

(57) ABSTRACT

Provided herein, in some embodiments, are systems, methods, compositions, and kits for detecting and quantifying analytes using a primary analyte binding molecule conjugated to a nucleic acid template.

14 Claims, 14 Drawing Sheets

(56) References Cited

U.S. PATENT DOCUMENTS

2015/0293021 A1* 10/2015 Finkelstein ........ G01N 21/6452
   506/13
2018/0195950 A1* 7/2018 Tsay .................... C09D 133/26

OTHER PUBLICATIONS

Illumina Sequencing Overview, Illumina Presentation, Dec. 31, 2013, avail at https://www.well.ox.ac.uk/ogc/wp-content/uploads/2017/09/Illumina_Sequencing_Overview_15045845_D.pdf.*

Merriam-Webster, definition of adjacent, avail at https://www.merriam-webster.com/dictionary/adjacent, accessed Jul. 7, 2022.*

* cited by examiner

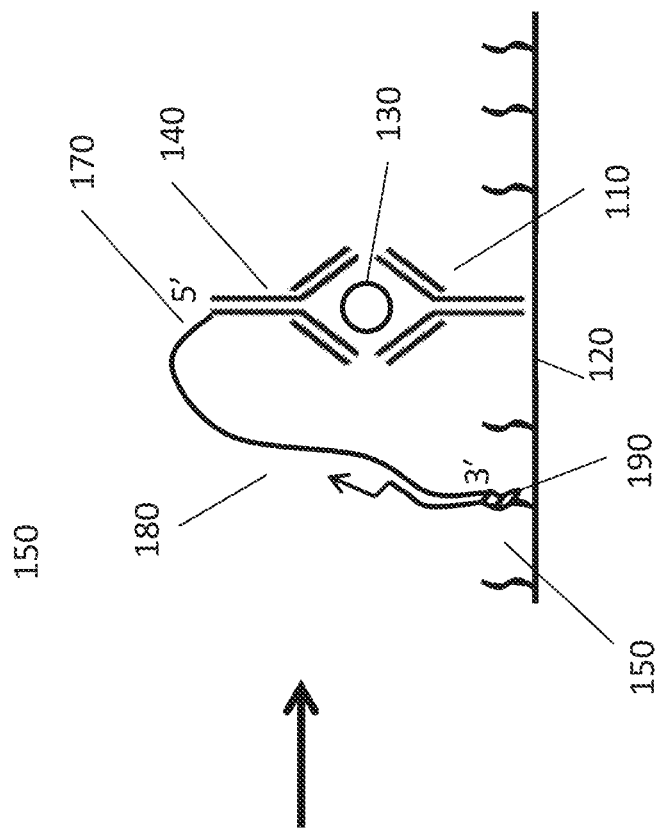
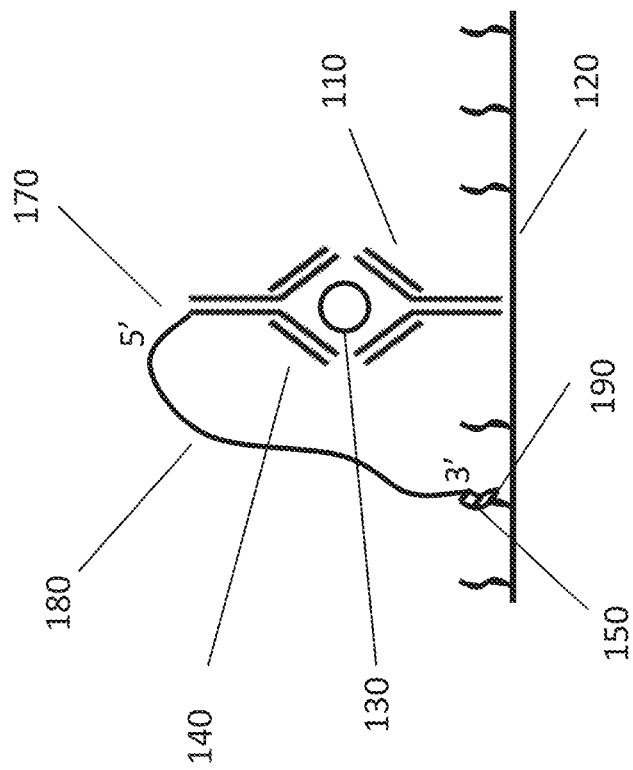
FIG. 1d
FIG. 1c

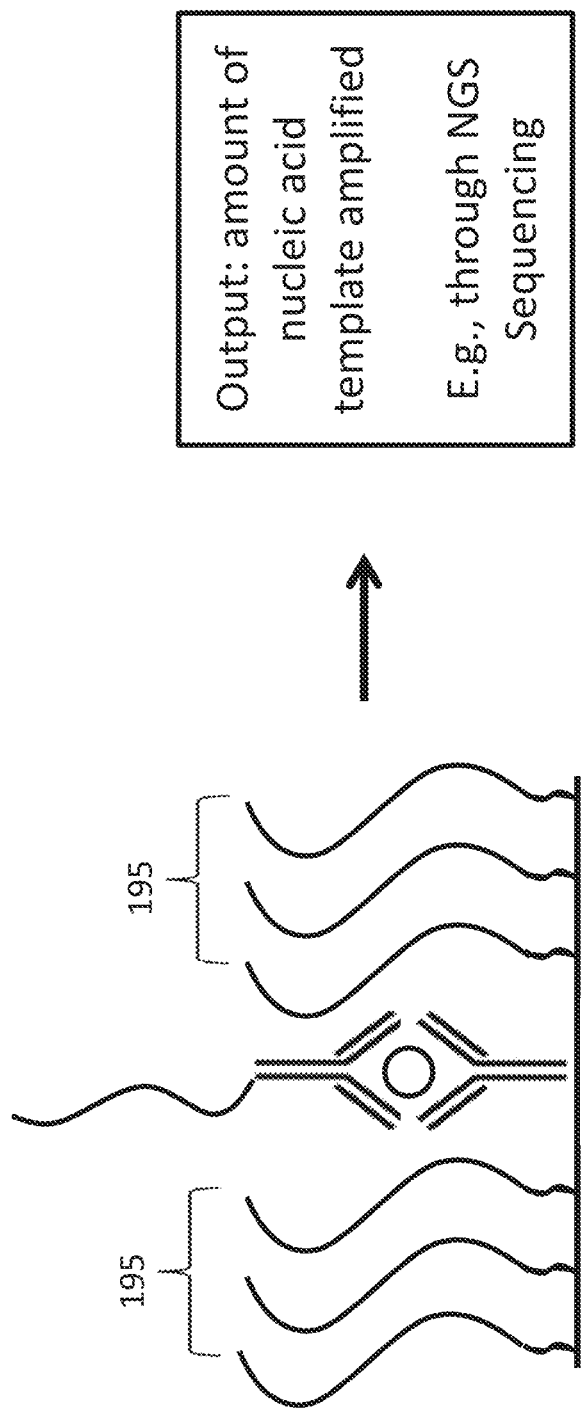

SYSTEMS AND METHODS FOR MULTIPLEXED ANALYTE DETECTION USING ANTIBODY-OLIGONUCLEOTIDE CONJUGATES

CROSS-REFERENCE TO RELATED APPLICATIONS

This application claims the benefit under 35 U.S.C. § 119(e) of the filing date of U.S. provisional patent application Ser. No. 62/626,637, entitled "Systems and Methods for Multiplexed Analyte Detection using Antibody-Oligonucleotide Conjugates," filed Feb. 5, 2018 and U.S. provisional patent application Ser. No. 62/641,191, entitled "Systems and Methods for Multiplexed Analyte Detection using Antibody-Oligonucleotide Conjugates," filed Mar. 9, 2018, the entire contents of which are incorporated herein by reference.

TECHNICAL FIELD

The embodiments disclosed herein are generally directed towards systems and methods for detecting and quantifying analytes using a primary analyte binding molecule. More specifically, there is a need for systems and methods for quantifying analytes in a sample using an antibody-oligonucleotide reporter complex to allow for a larger number of analytes to be detected and quantified at the same time.

BACKGROUND

Currently, there are two main technologies involving use of primary analyte binding molecules (e.g., antibodies) for multiplexed quantitation of analytes (e.g., protein/glycans/lectins/small molecules). The first more primitive methodology involves immobilizing capture antibodies to defined areas on a chip, followed by a typical capture ELISA, and completed using either chromogenic, chemiluminescent or fluorescent signal of quantitation. The other more recent technique is a bead-based assay where a capture antibody is immobilized on beads and a fluorescently labeled detection antibody is used for quantitation in a flow cytometry based assay. The biggest limitation of these techniques is that only a limited number of analytes that can be detected at one time due to the limited availability of fluorophores that can be used due to spectral overlap.

As such, there is a need for new techniques to simultaneously detect and quantify large numbers of analytes at the same time.

BRIEF SUMMARY

In accordance with various embodiments, a method of measuring the amount of analyte in a sample is provided, the method comprising the steps of contacting a sample comprising at least one analyte with at least one primary analyte binding molecule, wherein the primary analyte binding molecule is immobilized on a solid support; contacting at least one secondary analyte binding molecule with at least one analyte, wherein the 5' end of at least one nucleic acid template is conjugated to the at least one secondary analyte binding molecule; and wherein the at least one nucleic acid template comprises an oligonucleotide sequence at the 3' end that hybridizes to a primer, wherein the primer is immobilized at the 5' end on the solid support adjacent to each of the at least one primary analyte binding molecule; performing one or more nucleic acid amplification reactions on at least one nucleic acid template, so that nucleic acid colonies are generated; and then measuring the presence of the nucleic acid colonies to determine the amount of specified analyte in a sample.

In various embodiments, the primary analyte binding molecule may be an antibody, an antibody fragment, a Fab fragment, a Fab' fragment, a F(ab') 2 fragment, an scFv protein, an analyte specific trapping agent, nanoparticle, lectin or receptor. In various embodiments disclosed herein, the secondary analyte binding molecule may be an antibody, an antibody fragment, a Fab fragment, a Fab' fragment, a F(ab') 2 fragment, an scFv protein, an analyte specific trapping agent, nanoparticle, lectin or receptor.

In various embodiments, the solid support is a flat surface, a flow cell or a bead. In various embodiments, the flow cell has at least one peak region and one valley region. In various embodiments the primary analyte binding molecule is bound to the valley region of the flow cell. In various embodiments, the primer is bound at a higher position than said primary analyte binding molecule. In other embodiments the solid support is a bead.

In various embodiments, the primer is modified to reduce enzymatic digestion. Such modifications may include modifications to the phosphodiester backbone; modifications to the sugar ring; 3' capping with inverted thymidine; and modifications on the nucleotide bases.

In various embodiments, the nucleic acid template is modified to reduce enzymatic digestion. Such modifications may include modifications to the phosphodiester backbone; modifications to the sugar ring; 3' capping with inverted thymidine; and modifications on the nucleotide bases.

In various embodiments, the nucleic acid template at its 5' end further comprises an oligonucleotide sequence that is identical to the primer sequence.

In various embodiments, amplification of the nucleic acid template results in an amplification product that is the reverse mirror image of the nucleic acid template.

In various embodiments, the 5' end of a filler nucleic acid sequence is attached to the secondary analyte binding molecule and the 3' end of the filler nucleic acid sequence is attached the 5' end of the nucleic acid template sequence. In various embodiments, the filler sequence is double stranded.

In various embodiments, the amount of analyte in a sample is determined by the presence of a unique recognition sequence associated with a particular secondary analyte binding molecule.

In various embodiments, the amount of analyte in a sample is determined by the presence of the nucleic acid colonies in a specific region of the flow cell.

In various embodiments, the presence of nucleic acid colonies is measured using DNA sequencing methods.

In another aspect, a kit for measuring the amount of analyte in a sample is provided, the kit comprising (1) at least one primary analyte binding molecule configured to be immobilized on a solid support; (2) at least one primer configured to be immobilized on the solid support adjacent to each of the at least one primary analyte binding molecule; and (3) at least one secondary analyte binding molecule; wherein the 5' end of at least one nucleic acid template is conjugated to the at least one secondary analyte binding molecule; wherein the at least one nucleic acid template comprises an oligonucleotide sequence at the 3' end that hybridizes to the at least one primer.

In various embodiments, the primary analyte binding molecule is selected from the group consisting of: antibodies, antibody fragments, Fab fragments; Fab' fragments; F(ab')2 fragments; scFv proteins; or analyte specific trapping agents, nanoparticles, lectins or receptors. In various embodiments, the secondary analyte binding molecule is selected from the group consisting of: antibodies, antibody fragments, Fab fragments; Fab' fragments; F(ab')2 fragments; scFv proteins; or analyte specific trapping agents or nanoparticles.

In various embodiments, the solid support is a flow cell. In various embodiments, the flow cell has at least one peak region and one valley region. In various embodiments, the primary analyte binding molecule is bound to the valley region of the flow cell. In various embodiments the primer is bound at a higher position than said primary analyte binding molecule on the flow cell.

In various embodiments, the solid support is a bead.

In various embodiments, the primer is modified to reduce enzymatic digestion. In various embodiments the modification is selected from the group consisting of: modifications to phosphodiester backbone; modifications to the sugar ring; 3' capping with inverted thymidine; and modifications on the nucleotide bases In various embodiments, the nucleic acid template sequence is modified to reduce enzymatic digestion. In various embodiments the modification is selected from the group consisting of: modifications to phosphodiester backbone; modifications to the sugar ring; 3' capping with inverted thymidine; and modifications on the nucleotide bases.

In various embodiments, the nucleic acid template at its 5' end further comprises an oligonucleotide sequence that is identical to the primer sequence.

In various embodiments, amplification of the nucleic acid template results in an amplification product that is the reverse mirror image of the nucleic acid template In various embodiments, the 5' end of a filler nucleic acid sequence is attached to the secondary analyte binding molecule and the 3' end of the filler nucleic acid sequence is attached the 5' end of the nucleic acid template sequence. In various embodiments the filler sequence is double stranded.

In various embodiments, the amount of analyte in a sample is determined by the presence of a unique recognition sequence associated with a particular secondary analyte binding molecule.

In various embodiments the amount of analyte in a sample is determined by the presence of the nucleic acid colonies in a specific region of the flow cell.

In various embodiments, the presence of nucleic acid colonies is measured using DNA sequencing methods.

In a further aspect, a method of measuring the amount of analyte in a sample is provided. The system can comprise a source unit configured to house a sample comprising a least one analyte, the sample configured to contact at least one primary analyte binding molecule, and at least one secondary analyte binding molecule, wherein the 5' end of at least one nucleic acid template is conjugated to the at least one secondary analyte binding molecule, and wherein the at least one nucleic acid template comprises an oligonucleotide sequence at the 3' end. The system can further comprise a reaction unit configured to receive a solid support configured to include (1) at least one primer immobilized on the solid support at the primer 5' end and (2) the at least one primary analyte binding molecule immobilized on the solid support, wherein the at least one primer is immobilized adjacent to the at least one primary analyte binding molecule. The reaction unit can further be configured to receive the sample comprising the at least one analyte from the source unit, the at least one analyte configured to bind to the at least one primary analyte binding molecule. The reaction unit can further be configured to receive the at least one secondary analyte binding molecule from the source unit, the at least one secondary analyte binding molecule configured to bind to the at least one analyte, wherein the oligonucleotide sequence at the 3' end of the nucleic acid template hybridizes to the primer. The system can further comprise an amplification unit configured to perform one or more nucleic acid amplification reactions on the at least one nucleic acid template, so that nucleic acid colonies are generated. The system can further comprise an identification unit configured to identify the specific nucleic acid colony associated with the specific analyte to determine the amount of analyte in a sample.

BRIEF DESCRIPTION OF THE DRAWINGS

FIGS. 1a-1f depicts a method of measuring the amount of analyte in a sample in accordance with various embodiments.

DETAILED DESCRIPTION

Figure 1B:
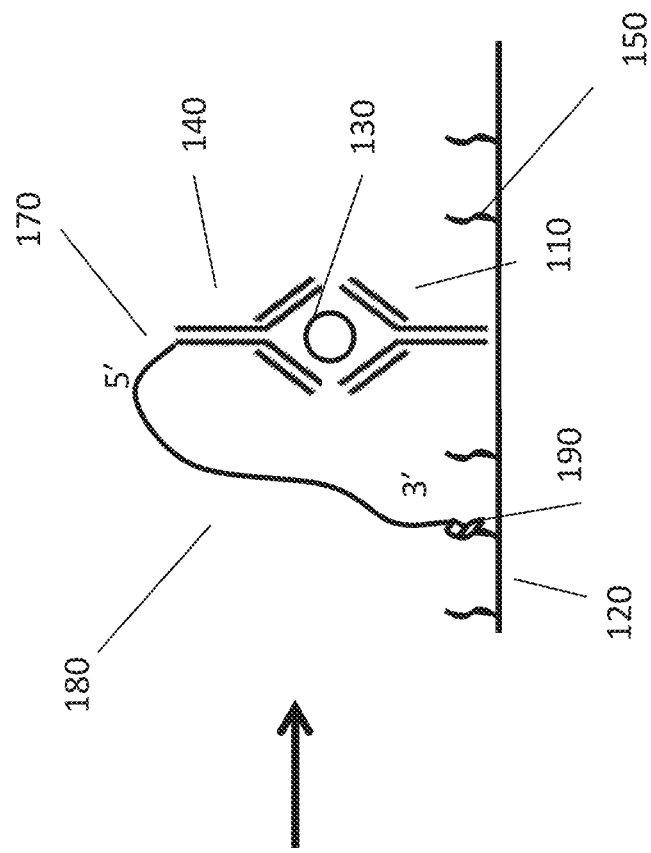

The following description of various embodiments is exemplary and explanatory only and is not to be construed as limiting or restrictive in any way. Other embodiments, features, objects, and advantages of the present teachings will be apparent from the description and accompanying drawings, and from the claims. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g. elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The term "nucleic acids" as used herein may include any polymer or oligomer (oligonucleotide) of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). The present disclosure contemplates any deoxyribonucleotide (DNA), ribonucleotide (RNA) or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Unless defined otherwise, all technical and scientific terms used herein have the same meaning as commonly understood by one of ordinary skill in the art to which the embodiments disclosed herein belongs. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

The phrase "next generation sequencing" (NGS) refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the MISEQ, HISEQ and NEXTSEQ Systems of Illumina and the Personal Genome Machine (PGM) and SOLiD Sequencing System of Life Technologies Corp, provide massively parallel sequencing of whole or targeted genomes. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing experiment performed to determine some information relating to at least one biomolecule (e.g., nucleic acid molecule).

DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "fragment library" refers to a collection of nucleic acid fragments, wherein one or more fragments are used as a sequencing template. A fragment library can be generated, for example, by cutting or shearing a larger nucleic acid into smaller fragments. Fragment libraries can be generated from naturally occurring nucleic acids, such as mammalian or bacterial nucleic acids. Libraries comprising similarly sized synthetic nucleic acid sequences can also be generated to create a synthetic fragment library.

In various embodiments, a sequence alignment method can align a fragment sequence to a reference sequence or another fragment sequence. The fragment sequence can be obtained from a fragment library, a paired-end library, a mate-pair library, a concatenated fragment library, or another type of library that may be reflected or represented by nucleic acid sequence information including for example, RNA, DNA, and protein based sequence information. Generally, the length of the fragment sequence can be substantially less than the length of the reference sequence. The fragment sequence and the reference sequence can each include a sequence of symbols. The alignment of the fragment sequence and the reference sequence can include a limited number of mismatches between the symbols of the fragment sequence and the symbols of the reference sequence. Generally, the fragment sequence can be aligned to a portion of the reference sequence to minimize the number of mismatches between the fragment sequence and the reference sequence.

In particular embodiments, the symbols of the fragment sequence and the reference sequence can represent the composition of biomolecules. For example, the symbols can correspond to identity of nucleotides in a nucleic acid, such as RNA or DNA, or the identity of amino acids in a protein. In various embodiments, the symbols can have a direct correlation to these subcomponents of the biomolecules. For example, each symbol can represent a single base of a polynucleotide. In other embodiments, each symbol can represent two or more adjacent subcomponents of the biomolecules, such as two adjacent bases of a polynucleotide. Additionally, the symbols can represent overlapping sets of adjacent subcomponents or distinct sets of adjacent subcomponents. For example, when each symbol represents two adjacent bases of a polynucleotide, two adjacent symbols representing overlapping sets can correspond to three bases of polynucleotide sequence, whereas two adjacent symbols representing distinct sets can represent a sequence of four bases. Further, the symbols can correspond directly to the subcomponents, such as nucleotides, or they can correspond to a color call or other indirect measure of the subcomponents. For example, the symbols can correspond to an incorporation or non-incorporation for a particular nucleotide flow.

In various embodiments, a computer program product can include instructions to select a contiguous portion of a fragment sequence; instructions to map the contiguous portion of the fragment sequence to a reference sequence using an approximate string matching method that produces at least one match of the contiguous portion to the reference sequence.

All publications mentioned herein are incorporated herein by reference for the purpose of describing and disclosing devices, compositions, formulations and methodologies which are described in the publication and which might be used in connection with the present disclosure.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

The practice of the present subject matter may employ, unless otherwise indicated, conventional techniques and descriptions of organic chemistry, molecular biology (including recombinant techniques), cell biology, and biochemistry, which are within the skill of the art.

I. Methods

In accordance with various embodiments, a method for measuring the amount of analytes in a sample is provided. A representative workflow is provided in the illustration of FIG. 1, which illustrates an exemplary workflow for implementing the methods disclosed herein.

Figure 1A:
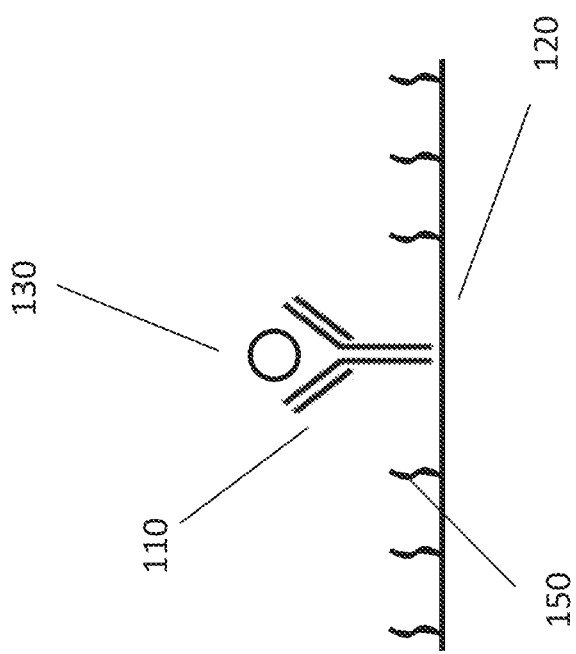

Referring to FIG. 1, a sample that contains at least one analyte 130 is contacted with at least one primary analyte binding molecule 110. As depicted in FIG. 1, the primary analyte binding molecule 110 may be an antibody bound to a solid support 120.

Next, a secondary analyte binding molecule 140 binds with the analyte 130, and the secondary analyte binding molecule 140 is bound to the 5' end 170 of a nucleic acid template 180. The 3' end 190 of the nucleic acid template comprises an oligonucleotide sequence configured to hybridize to a primer 150. The primer 150 can also be immobilized on the solid support 120, as illustrated in FIG. 1, adjacent to the at least one primary analyte binding molecule 110. In various embodiments, and as depicted for example in FIG. 1, a plurality of primers 150 is immobilized on the solid support 120 adjacent to the primary analyte binding molecule 110.

Next the oligonucleotide sequence on the 3' end of the nucleic acid template 180 hybridizes with the immobilized primer 150, and one or more amplification reactions on the nucleic acid template are performed. As a result nucleic acid colonies 195 are generated.

The sample can be any sort of fluid mixture that contains at least one analyte to measure. The sample can be, for example, a biological sample. Such biological samples can include, but are not limited to, blood, plasma, cerebrospinal fluid, saliva. Biological samples may include further processing using known techniques in the art before an analyte in said sample is measured.

The primary analyte binding molecule can be any molecule that recognizes and binds with a specific analyte. Examples of such molecules include antibodies, antibody fragments, Fab fragments, Fab' fragments, F(ab')2 fragments, scFv proteins, analyte specific trapping agents, nanoparticles, lectins or receptors. It can be helpful for the primary analyte binding molecule to have a high affinity and specificity for its analyte. These molecules can be made using conventional and known techniques in the art, or may be purchased commercially. The primary analyte binding molecule (or molecules) can be immobilized on a solid support using known techniques in the art. The primary analyte binding molecules can be bound to a variety of solid support surfaces, and the immobilization technique can depend upon the type of solid support used. See e.g., Kim and Herr Biomicrofluidics 7, 41501 (2013). The primary analyte binding molecule can also be immobilized on the solid support in such a way that it does not affect the molecule's binding affinity or specificity for its target analyte. Such methods are known in the art and include physisorption, bioaffinity immobilization and covalent bonding.

The secondary analyte binding molecule can be any molecule that recognizes and binds with a specific analyte. Examples of such molecules also include antibodies, antibody fragments, Fab fragments, Fab' fragments, F(ab') 2 fragments, scFv proteins, analyte specific trapping agents, nanoparticles, lectins or receptors. The secondary analyte binding molecule may have the same or different general structure as the primary analyte binding molecule. For example, the primary analyte binding molecule might be an antibody, whereas the secondary analyte binding molecule might be a scFv fusion protein. In various embodiments, the primary and secondary analyte binding molecules are identical except that the primary analyte binding molecule is immobilized on a solid support, and the secondary analyte binding molecule is conjugated to a nucleic acid template. In various embodiments, the primary and secondary analyte binding molecules are two different species of the same class of molecule. For example, the primary analyte binding molecule can be a first species of antibody and the secondary analyte binding molecule can be a second species of antibody. It should be understood, however, that both the primary and secondary analyte binding molecules should be capable of binding to the same analyte concurrently. It can be helpful for the secondary analyte binding molecule (and the primary analyte binding molecule as mentioned above) to have a high affinity and specificity for its analyte.

Systems, methods, and compositions described herein encompass a primary analyte binding molecule (or molecules) and/or a secondary analyte binding molecule (or molecules) that is free in solution. In some embodiments, the primary analyte binding molecule is free in solution. In some embodiments, the primary analyte binding molecule is not immobilized on a solid support. In some embodiments, the primary analyte binding molecule is immobilized on a solid support. In some embodiments, the secondary analyte binding molecule is free in solution. In some embodiments, the secondary analyte binding molecule is not immobilized on a solid support. In some embodiments, the secondary analyte binding molecule is immobilized on a solid support.

In some embodiments, the primary analyte binding molecule is immobilized on a solid support and the secondary analyte binding molecule is not immobilized on a solid support. In some embodiments, the primary analyte binding molecule is not immobilized on a solid support and the secondary analyte binding molecule is immobilized on a solid support. In some embodiments, the primary analyte binding molecule and the secondary analyte binding molecule are immobilized on a solid support. In some embodiments, the primary analyte binding molecule and the secondary analyte binding molecule are not immobilized on a solid support.

In some embodiments, a nucleic acid template (discussed in more detail below) can be conjugated to the primary analyte binding molecule. In various embodiments, a nucleic acid template (discussed in more detail below) can be conjugated to the secondary analyte binding molecule. This conjugation can occur in such a way so as not to significantly reduce the binding affinity and specificity of the primary analyte binding molecule or the secondary analyte binding molecule. Further conjugation can be done in such a way that it does not affect the nucleic acid template's ability to hybridize for subsequent PCR amplification. Such techniques for conjugation of a nucleic acid template to an analyte binding molecule are conventional and well known in the art. See, e.g. Kazane et al. (2012) PNAS, 109(10): 3731-3736.

Figure 7:
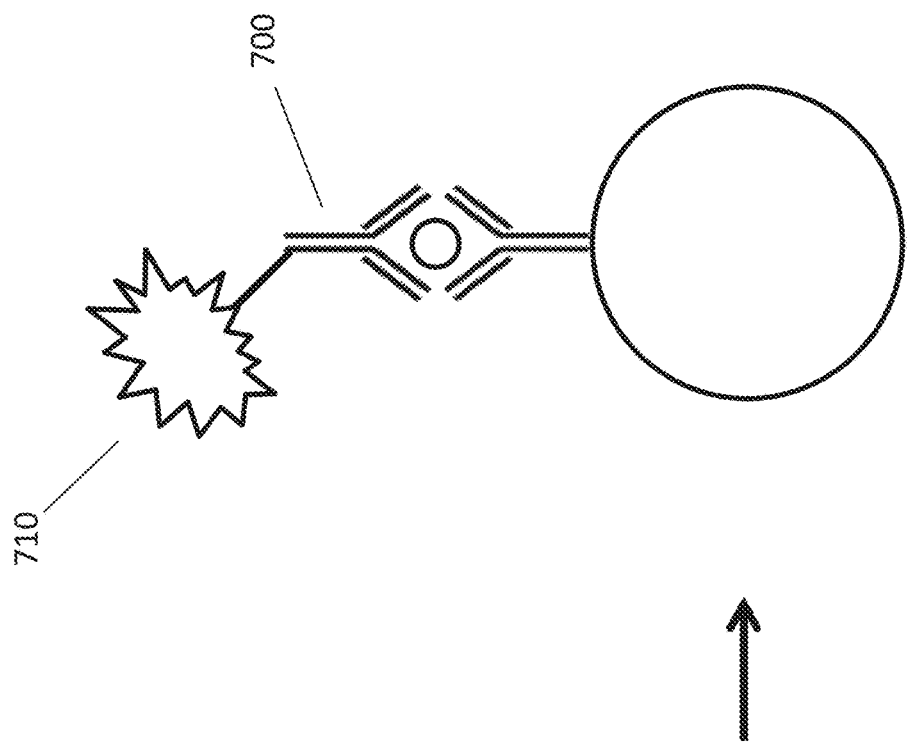
FIG. 7 depicts use of a secondary-antibody (Ab) enzyme complex to measure analyte in the sample when bound to an analyte that is also bound to a primary antibody in accordance with various embodiments.
Figure 7:
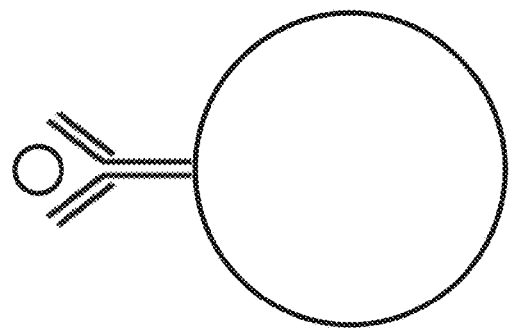
Figure 8:
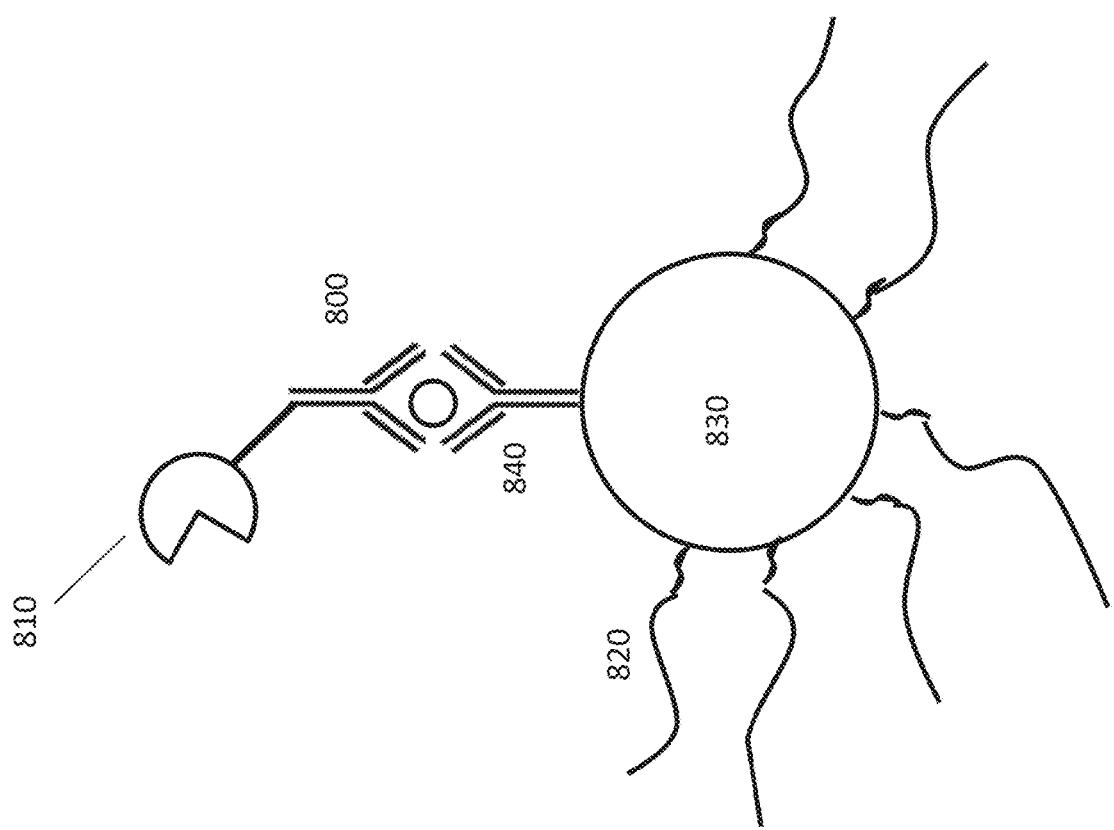
FIG. 8 depicts a secondary analyte binding molecule bound to a polymerase complex in accordance with various embodiments.

In various embodiments, such as that illustrated, for example, in FIG. 7, instead of being bound to a nucleic acid template, the secondary analyte binding complex molecule 700 can be conjugated to an enzyme 710 that can be readily visualized (e.g. horseradish peroxidase or alkaline phosphatase). In other various embodiments, for example such as that illustrated in FIG. 8, the secondary analyte binding molecule 800 is conjugated to a polymerase 810. The primary analyte binding 840 and at least one unique oligonucleotide sequence 820 are bound to a solid support 830. Detection in this embodiment occurs in two phases. First, an amplification reaction is initiated on the polymerase 810. The resulting hydrogen ions released by this reaction are measured to indicate the presence of an analyte in the analyte binding complex. Second, the oligonucleotide sequence 820, is sequenced to provide the identity of the analyte using a sequencing platform such as the Ion Torrent system.

Figure 11:
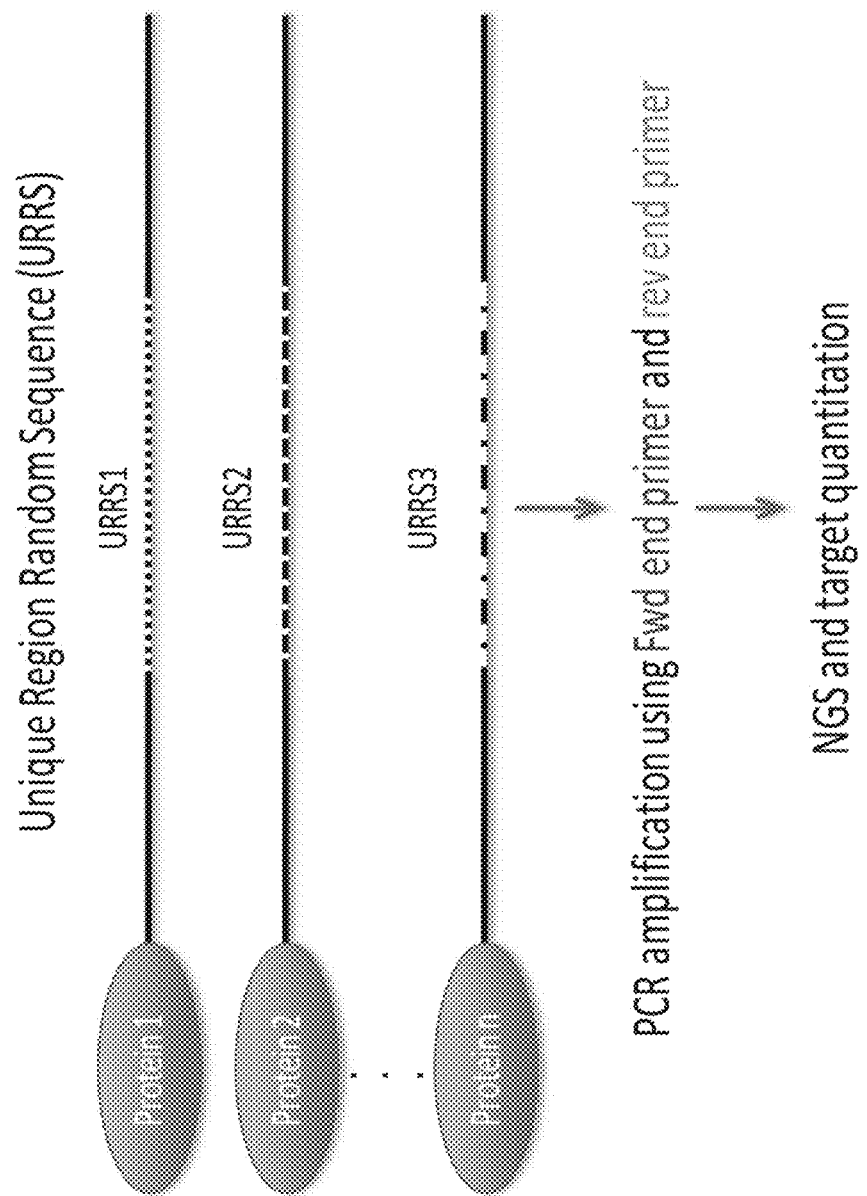
FIG. 11 depicts a primer comprising a forward end primer, a reverse end primer, and an unique region random sequence (URRS) bound to a protein (e.g., an antibody) in accordance with various embodiments.

In some embodiments, such as that illustrated, for example, in FIG. 11, the secondary analyte binding molecule can be conjugated to a nucleic acid template. In some embodiments, the nucleic acid template comprises a forward end primer, a reverse end primer, and a unique region random sequence (URRS). In some embodiments, the nucleic acid template is detected by amplifying the detection oligo and/or sequencing the amplified detection oligo.

In some embodiments, the present disclosure provides a method of measuring the amount of analyte in a sample comprising the steps of (a) contacting a sample comprising at least one analyte with at least one primary analyte binding molecule; wherein the analyte binds to the at least one primary analyte binding molecule; (b) contacting at least one secondary analyte binding molecule with the at least one analyte, wherein the 5' end of at least one nucleic acid template is conjugated to the at least one secondary analyte binding molecule; and wherein the at least one nucleic acid template comprises an oligonucleotide sequence at the 3' end that hybridizes to a primer; wherein the at least one nucleic acid template comprises a unique region random sequence (URRS); (c) hybridizing the oligonucleotide sequence to the primer; (d) performing one or more nucleic acid amplification reactions on the at least one nucleic acid template, so that nucleic acid colonies are generated; and measuring the presence of the nucleic acid colonies to determine the amount of the specified analyte in a sample.

In some embodiments, the nucleic acid template is detected by amplifying the nucleic acid template using primers that are complementary to the forward end primer and/or reverse end primer. In some embodiments, the nucleic acid template is detected by sequencing the amplified nucleic acid template using primers that are complementary to the forward end primer and/or reverse end primer. In some embodiments, the nucleic acid template is detected by amplifying the nucleic acid template and sequencing the amplified nucleic acid template using primers that are complementary to the forward end primer and/or reverse end primer.

A nucleic acid template may be amplified using any suitable method. In some embodiments, the nucleic acid template is amplified using polymerase chain reaction (PCR). In some embodiments, the nucleic acid template is amplified using quantitative PCR (qPCR). In some embodiments, the nucleic acid template is detected using real-time quantitative PCR (RT-PCR).

A nucleic acid template may be sequenced using any suitable method. In some embodiments, the nucleic acid template (e.g., an amplified nucleic acid template) is sequenced using massively parallel sequencing. In some embodiments, the nucleic acid template is sequenced using high-throughput sequencing. In some embodiments, the nucleic acid template is sequenced using next generation sequencing (NGS).

A nucleic acid template may comprise any length unique region random sequence (URRS). In some embodiments, the URRS is 10-100 nucleotides in length. In some embodiments, the URRS is 20-100 nucleotides, 30-100 nucleotides, 40-100 nucleotides, 50-100 nucleotides, 60-100 nucleotides, 70-100 nucleotides, 80-100 nucleotides, or 90-100 nucleotides in length. In some embodiments, the URRS is 10-90 nucleotides, 10-80 nucleotides, 10-70 nucleotides, 10-60 nucleotides, 10-50 nucleotides, 10-40 nucleotides, 10-30 nucleotides, or 10-20 nucleotides in length.

In some embodiments, the nucleic acid template comprises an URRS having minimal secondary structure (e.g., hairpin). In some embodiments, the nucleic acid template comprises an URRS that is not complementary to a primer sequence. In some embodiments, the nucleic acid template comprises an URRS that is not amplified by a primer sequence.

Nucleic acid template as used herein can be an entity which comprises the nucleic acid to be amplified or sequenced in single-stranded form. As outlined below the nucleic acid to be amplified or sequenced can also be in double stranded form. Thus, nucleic acid templates of the embodiments disclosed herein may be single or double stranded nucleic acids. The nucleic acid templates can be of variable lengths. They can be at least 50 nucleotides in length and preferably 150 to 400 nucleotides in length. The nucleotides making up the nucleic acid templates may be naturally occurring or non-naturally occurring nucleotides. The nucleic acid templates can not only comprise the nucleic acid to be amplified but may in addition contain at the 5' and 3' end short oligonucleotide sequences (i.e., primers).

The oligonucleotide sequence contained at the 3' end of the nucleic acid can be of any sequence and any length. Suitable lengths and sequences of oligonucleotide can be selected using methods well-known and documented in the art. In various embodiments, the oligonucleotide sequence contained at the 3' end of the nucleic acid template discussed herein can be at least five nucleotides in length, preferably between 5 and 100 nucleotides in length and more preferably approximately 20 nucleotides in length. This sequence may contain naturally occurring and/or non-naturally occurring nucleotides. In various embodiments, the 3' end oligonucleotide sequence of the nucleic acid template can be designed to hybridize with a primer that is immobilized on the solid support.

In various embodiments, the nucleic acid template comprises an oligonucleotide sequence at the 5' end. The sequence of the 5' end oligonucleotide can be the same as the sequence of the primer. The 5' end oligonucleotide can be of any sequence and of any length. Suitable lengths and sequences of oligonucleotide can be selected using methods well known and documented in the art. In accordance with various embodiments, the length of the 5' end oligonucleotide can be at least 5 nucleotides in length, preferably between 5 and 100 nucleotides in length and more preferably of approximately 20 nucleotides in length. Naturally occurring or non-naturally occurring nucleotides may be present in the 5' oligonucleotide sequence.

The oligonucleotide sequences contained at the 5' and 3' end respectively of a nucleic acid template need not be located at the extreme ends of the template. For example although the oligonucleotide sequences are preferably located at or near the 5' and 3' ends (or termini) of the nucleic acid template (for example within 0 to 100 nucleotides of the 5' and 3' termini), they may be located further away (e.g. greater than 100 nucleotides) from the 5' or 3' termini of the nucleic acid template. The oligonucleotide sequences may therefore be located at any position within the nucleic acid template providing the sequences are on either side, i.e. flank, the nucleic acid sequence which is to be amplified.

Nucleic acid template as used herein can also include an entity which comprises the nucleic acid to be amplified or the sequence in a double-stranded form. When the nucleic acid template is in double stranded form, the oligonucleotide sequences are contained at the 5' and 3' ends respectively of one of the strands. The other stand, due to the base pairing rules of DNA, is complementary to the strand containing the oligonucleotide sequences.

Figure 2:
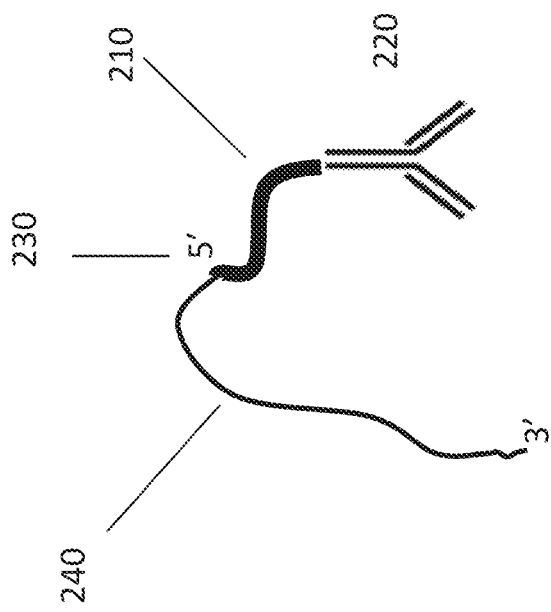
FIG. 2 depicts a secondary analyte binding molecule conjugated with a nucleotide template sequence in accordance with various embodiments. The secondary analyte binding molecule may be reversibly bound to the DNA conjugate.

As depicted in FIG. 2, a filler sequence 210 may also be present between the 5' end 230 of the nucleic acid template sequence 240 and the secondary analyte binding molecule 220. This filler sequence may be of any size and of any sequence as long as the 3' oligonucleotide sequence within the nucleic acid template can hybridize to the primer sequence immobilized to the solid support. This filler may also be double stranded or single stranded. The nucleic acid templates may be prepared using techniques which are standard or conventional in the art. Generally these will be based on genetic engineering techniques.

The nucleic acids to be amplified can be obtained using methods well known and documented in the art. For example, a nucleic acid sample such as total DNA, genomic DNA, cDNA, total RNA, mRNA can be obtained by methods well known and documented in the art, and fragments can be generated therefrom by, for example, limited restriction enzyme digestion or by mechanical means.

The nucleic acid template may be modified to prevent or reduce enzymatic digestion. Such modifications can include, for example, modifications to the phosphodiester backbone; modifications to the sugar ring; 3' capping with inverted thymidine; and modifications on the nucleotide bases.

The nucleic acid template can be amplified by the hybridization of the oligonucleotide sequence on its 3' end to a primer, which can be immobilized on a solid support. The primer can be an entity comprising an oligonucleotide sequence capable of hybridizing to a complementary sequence and initiating a specific polymerase reaction. The sequence comprising the primer can be chosen to help maximize hybridizing activity with its complementary sequence and very low non-specific hybridizing activity to any other sequence. Examples of primers suitable for this use are well known in the art. The primer can be 5 to 100 bases in length. Alternatively, the primer can be 15 to 25 bases in length. Naturally occurring or non-naturally occurring nucleotides may be present in the primer. One or more different primers may be used to generate nucleic acid colonies in the methods disclosed herein.

The primers may be prepared using techniques which are standard or conventional in the art. Generally, the primers can be synthetic oligonucleotides generated by methods well known and documented in the art, or may be purchased from commercial sources.

The 5' end of the primer can be modified to carry a means for attaching the primer covalently to a solid support. Such a means can include, for example, a chemically modifiable functional group, such as, for example a phosphate group, a carboxylic or aldehyde moiety, a thiol, or an amino group. In particular, the thiol, phosphate or amino group can be used for 5'-modification of the nucleic acid.

Immobilization of a primer to a support by the 5' end leaves its 3' end remote from the support such that the primer is available for chain extension by a polymerase once hybridization with a complementary oligonucleotide sequence contained at the 3' end of the nucleic acid template has taken place.

If desired, the primers can be designed to include additional desired sequences such as, for example, restriction endonuclease sites or other types of cleavage sites each as ribozyme cleavage sites. Other desirable sequences include fold-back DNA sequences (which form hairpin loops or other secondary structures when rendered single-stranded), 'control' DNA sequences which direct a protein/DNA interaction, such as, for example, a promoter DNA sequence, which is recognized by a nucleic acid polymerase or an operator DNA sequence, which is recognized by a DNA-binding protein.

Primers can also be modified to prevent enzymatic digestion. Such modifications can include modifications to the phosphodiester backbone, modifications to the sugar ring, 3' capping with inverted thymidine, and modifications on the nucleotide bases.

One or more different primers can be used to amplify any nucleic acid sequence. This contrasts with and has an advantage over many of the amplification methods known in the art such as where different specific primers may be designed for each particular nucleic acid sequence to be amplified.

As stated above, both the at least one primary analyte binding molecule and at least one primer can be bound to a solid support. The solid support can be any solid surface to which nucleic acids can be covalently attached, such as, for example, latex beads, dextran beads, polystyrene, polypropylene surface, polyacrylamide gel, metal surfaces (e.g., gold, aluminum, titanium), microplates, well plates, chips, microarrays flow cells, glass surfaces, slides and silicon wafers. Nucleic acids may be attached to a solid support using any chemical or non-chemical attachment method including chemically-modifiable functional groups. Nucleic acid sequences and/or analyte binding molecules can be attached, or immobilized, on solid supports via irreversible passive adsorption or via affinity between molecules (for example, immobilization on an avidin-coated surface by biotinylated molecules). In various embodiments, the attachment is of sufficient strength that it cannot be removed by washing with water or aqueous buffer under DNA-denaturing conditions.

Figure 3:
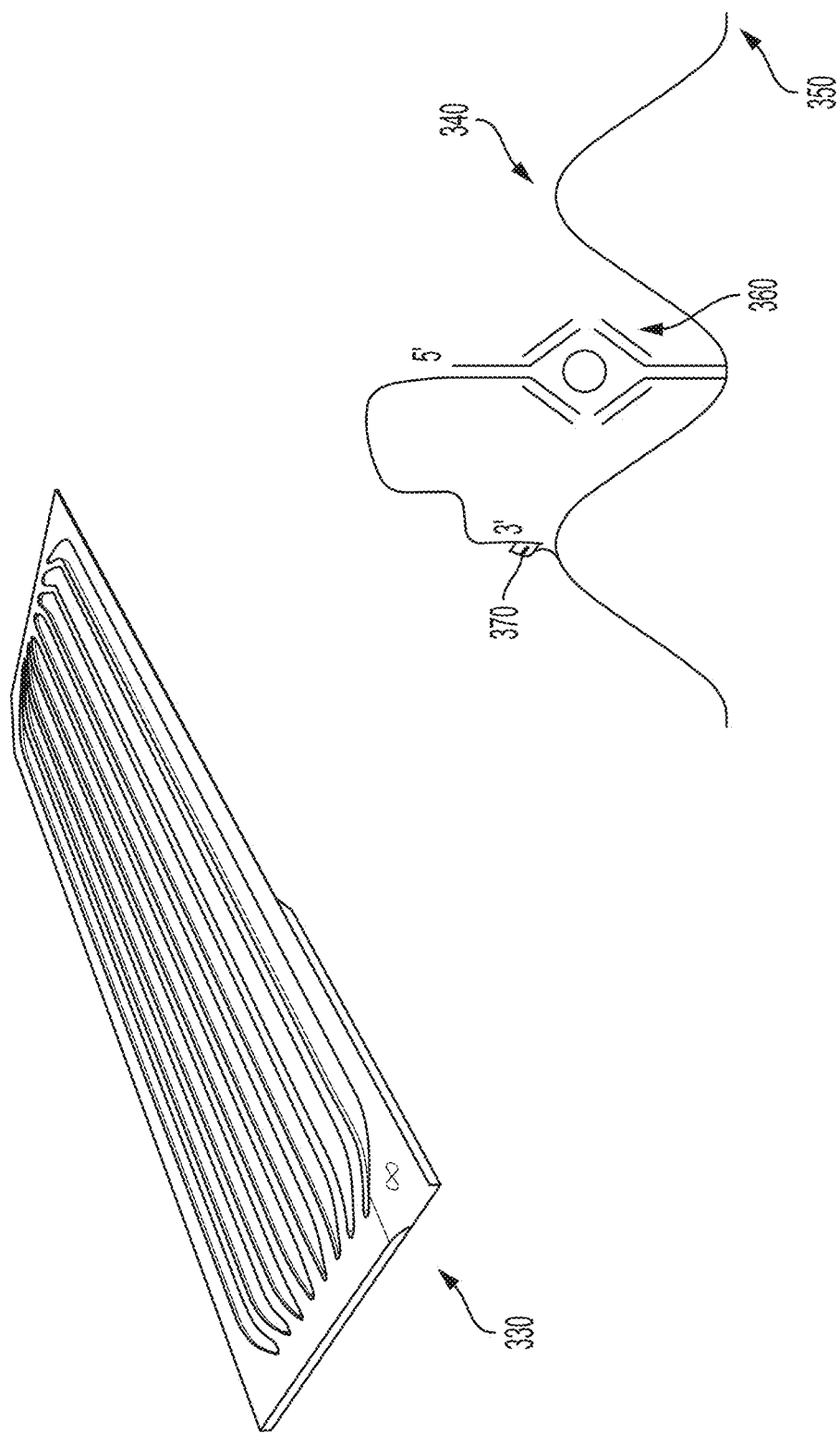
FIG. 3 depicts an analyte binding complex attached to a flow cell in accordance with various embodiments. In this embodiment there is etching on the flow cell to enable primary analyte binding molecules to be fixed irreversibly within the valley of flow cell. The immobilized primer is at a higher position, called the peak.

In various embodiments, the solid support can be a flat surface such as a chip, slide, microarray or a flow cell. In various embodiments, the solid support surface is flat but has at least one peak and at least one valley provided (for example, etched) on its surface. FIG. 3 illustrates one example of this with a solid support 330 comprising a peak 340 and valley 350. As further illustrated, solid support 330 can have a plurality of peak/valley combinations in the form of, for example, wells, through-holes, lanes, and so on. In various embodiments, as further illustrated in FIG. 3, a primary analyte binding molecule 360 is immobilized on the solid surface 330 in valley 350. In various embodiments, the primer can be immobilized on the solid surface at a point higher than the primary analyte binding molecule. This is illustrated, for example in FIG. 3 with primer 370 immobilized on peak 340 of solid surface 330. This configuration is advantageous in that it is easier for the 3' end oligonucleotide of the nucleic acid template to hybridize with the primer.

Figure 9:
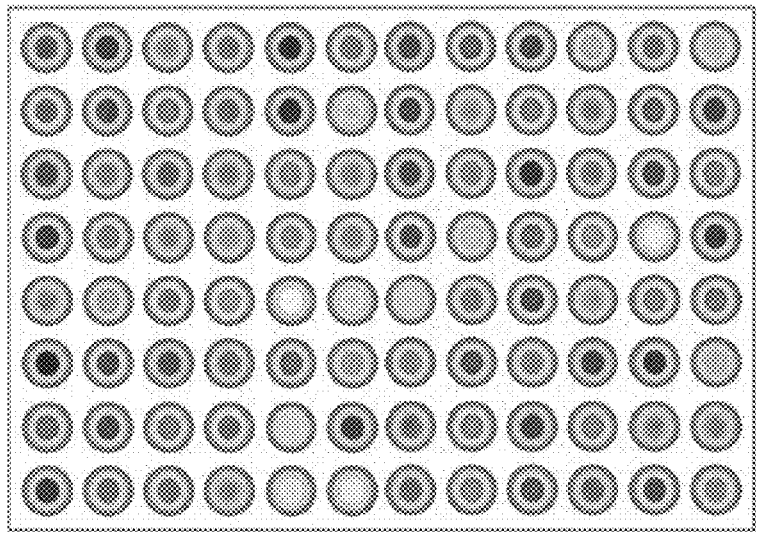
FIG. 9 depicts a primary analyte binding molecule bound to unique colored bead in accordance with various embodiments.
Figure 9:
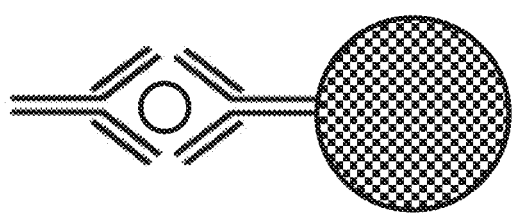
Figure 9:
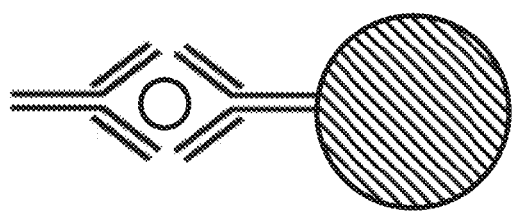
Figure 9:
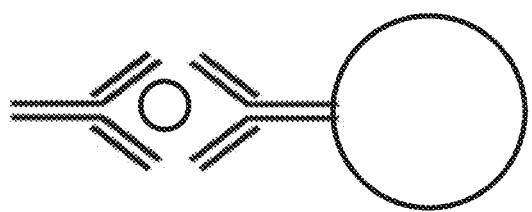

In various embodiments, the solid surface is a bead (See FIGS. 6-9). Referring the FIG. 6, bead 600 can include a unique primary analyte binding molecule 610 and a plurality of primers 620. As such, the bead 600 allows an analyte 630, and then a secondary analyte binding molecule 640 to complex with the primary analyte binding molecule 610 immobilized on bead 600. Amplification reactions can then occur when the 3' end oligonucleotide sequence of a nucleic acid template 650 conjugated to secondary analyte binding molecule 640 hybridizes with the primer 620 immobilized on the bead 600. In various embodiments, the primary analyte binding molecules may be immobilized on beads of different colors depending on the analyte for which they bind. Referring to FIG. 9, such beads may subsequently be used to determine the presence of a given analyte based on the color of the bead to which that analyte is bound.

Once both the primary analyte binding molecules and primers have been synthesized, they are mixed together in appropriate proportions so that when they are attached to the solid support an appropriate density of attached primary analyte binding molecules and primers is obtained. The percentage of primers in the mixture can be higher than the percentage of primary analyte binding molecules. The ratio of primers to primary analyte binding molecules can be such that when the primers and primary analyte binding molecules are immobilized to the solid support, a plurality of primers (or lawn of primers) is formed wherein the primers can be located at an approximately uniform density over the whole or a defined area of the solid support, with one or more primary analyte binding molecules being immobilized individually at intervals within the lawn of primers.

Figure 5:
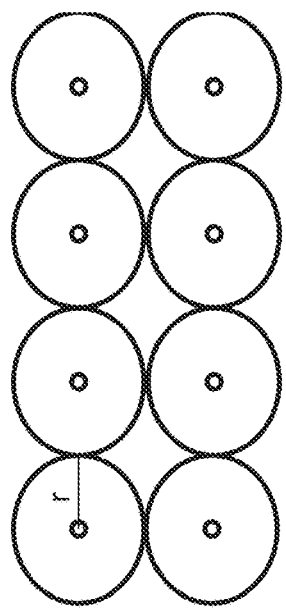
FIG. 5 is a top view of spatial separation between antibodies in accordance with various embodiments.
Figure 4:
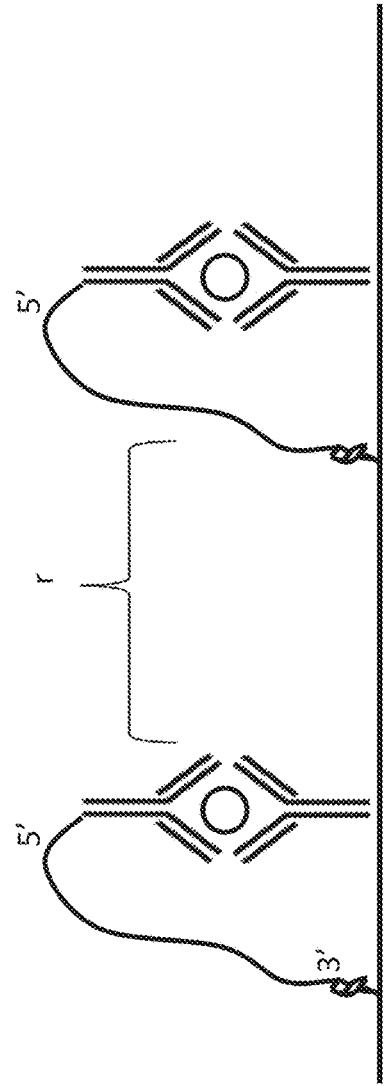
FIG. 4 is a side view of spatial separation between the primary antibodies in accordance with various embodiments.
Figure 6:
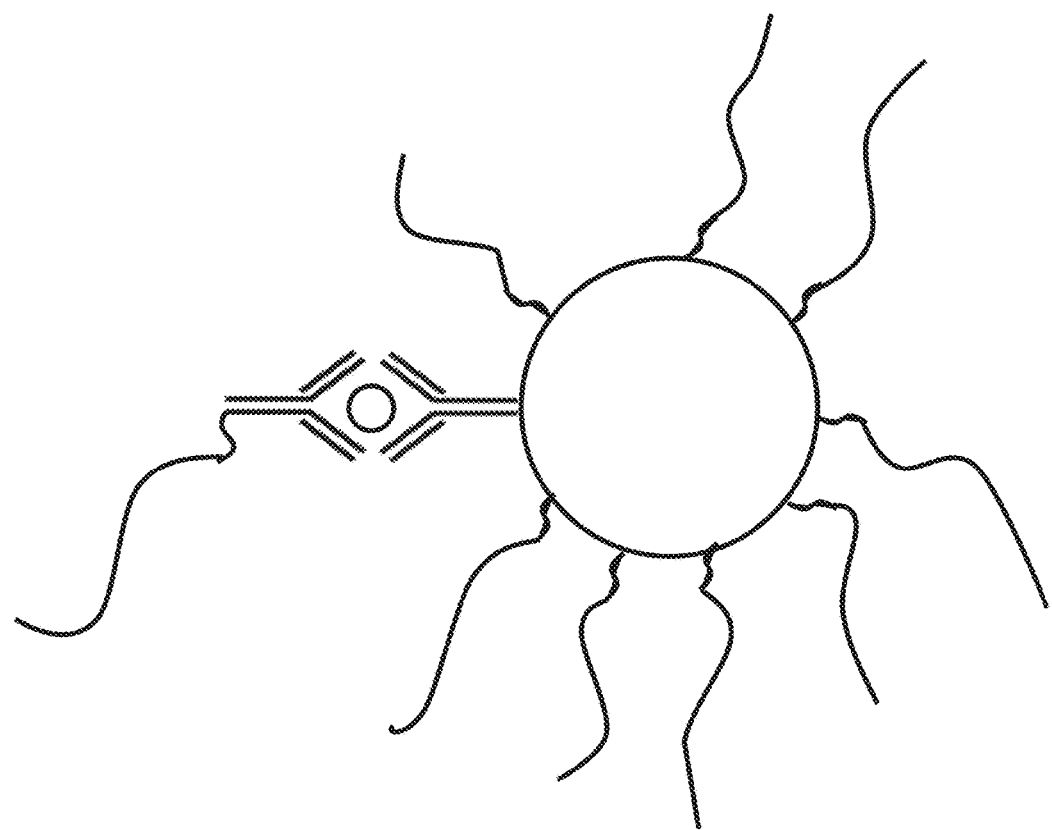
FIG. 6 depicts a secondary-antibody (Ab)-Oligo bound to an analyte which is also bound to a primary antibody immobilized on a bead in accordance with various embodiments.
Figure 6:
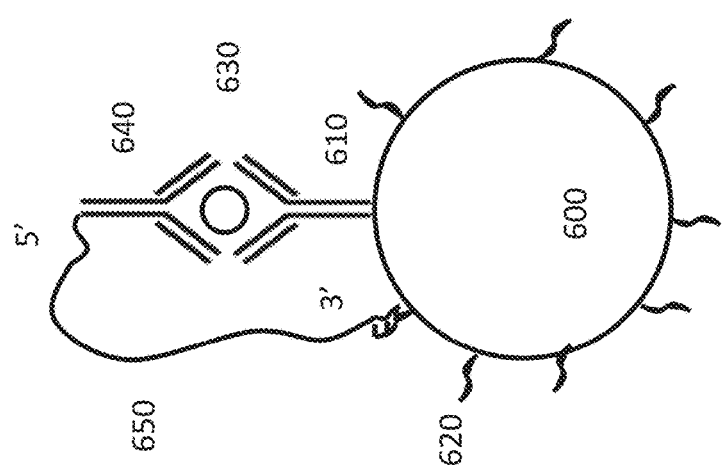

As shown in FIGS. 4 and 5, in various embodiments the distance between the primary analyte binding molecules is twice the length of the filler sequence and the nucleic acid template sequence. The distance between the individual primers and the individual primary analyte binding molecules (and hence the density of the primers and primary analyte binding molecules) can be controlled by altering the concentration of primers and primary analyte binding molecules that are immobilized to the support. A preferred density of primers is at least 1 fmol/mm$^2$, preferably at least 10 fmol/mm$^2$, more preferably between 30 to 60 fmol/mm$^2$. The density of nucleic acid templates for use in the methods disclosed herein is typically 10,000/mm$^2$ to 100,000/mm$^2$. It is believed that higher densities, for example, 100,000/mm$^2$ to 1,000,000/mm$^2$ and 1,000,000/mm$^2$ to 10,000,000/mm$^2$ may be achieved.

Controlling the density of attached primary analyte binding molecules and primers in turn allows the final density of nucleic acid colonies on the surface of the support to be controlled. This is due to the fact that, in accordance with various embodiments, one nucleic acid colony can result from the attachment of one nucleic acid template, providing the primers are present in a suitable location on the solid support (see in more detail below). The density of nucleic acid molecules within a single colony can also be controlled by controlling the density of attached primers.

Therefore, the various embodiments herein allow for the generation of a nucleic acid colony from a single nucleic acid template conjugated to a secondary analyte binding molecule of an analyte complex, and that the size of these colonies can be controlled by altering the number of rounds of amplification that the nucleic acid template is subjected to. Thus the number of nucleic acid colonies formed on the surface of the solid support is dependent upon the number of nucleic acid templates which are initially bound to a secondary analyte molecule which is bound to an analyte bound to a primary analyte binding molecule, providing there is a sufficient number of immobilized primers within the locality of each immobilized analyte complex. Therefore in may be preferable to immobilize primers and primary analyte binding molecules to a solid support comprising a lawn of immobilized primers at an appropriate density with primary analyte binding molecules at intervals within the lawn of primers.

Such so called "autopatterning" of nucleic acid colonies has an advantage over many methods of the prior art in that a higher density of nucleic acid colonies can be obtained due to the fact that the density can be controlled by regulating the density at which the nucleic acid templates are originally immobilized. Such a method is thus not limited by, for example, having specifically to array specific primers on particular local areas of the support and then initiate colony formation by spotting a particular sample containing nucleic acid template on the same local area of primer. The numbers of colonies that can be arrayed using prior art methods, for example those disclosed in WO96/04404 (Mosaic Technologies, Inc.) is thus limited by the density/spacing at which the specific primer areas can be arrayed in the initial step.

By being able to control the initial density of the nucleic acid templates and hence the density of the nucleic acid colonies resulting from the nucleic acid templates, together with being able to control the size of the nucleic acid colonies formed and in addition the density of the nucleic acid templates within individual colonies, an optimum situation can be reached wherein a high density of individual nucleic acid colonies can be produced on a solid support of a large enough size and containing a large enough number of amplified sequences to enable subsequent analysis or monitoring to be performed on the nucleic acid colonies.

In accordance with various embodiments, the covalent binding of the primers and primary analyte binding molecule (s) to the solid support can be induced by a crosslinking agent such as for example 1-ethyl-3-(3-dimethylaminopropyl)-carbodiimide hydrochloride (EDC), succinic anhydride, phenyldiisothiocyanate or maleic anhydride, or a hetero-bifunctional crosslinker such as for example m-maleimidobenzoyl-N-hydroxysuccinimide ester (MBS), N-succinimidyl[4-iodoacethyl]aminobenzoate (SIAB), Succinimidyl 4-[N-maleimidomethyl]cyclohexane-1-carboxylate (SMCC), N-γ-maleimidobutyryloxy-succinimide ester (GMBS), Succinimidyl-4-[p-maleimidophenyl]butyrate (SMPB) and the sulfo (water-soluble) corresponding compounds. The preferred crosslinking reagents for use in the embodiments disclosed herein, are s-SIAB, s-MBS and EDC.

In accordance with various embodiments, the attachment of primers and primary analyte binding molecules to a solid support should generally not be affected by either the exposure to high temperatures and the repeated heating/cooling cycles employed during the nucleic acid amplification procedure. Moreover the support should allow the obtaining of a density of attached primers of at least 1 fmol/mm$^2$, preferably at least 10 fmol/mm$^2$, more preferably between 30 to 60 fmol/mm$^2$.

The covalent binding of the primers to the solid support can be carried out using techniques which are known and documented in the art. For example, epoxysilane-amino covalent linkage of oligonucleotides on solid supports such as porous glass beads has been widely used for solid phase in situ synthesis of oligonucleotides (via a 3' end attachment) and has also been adapted for 5' end oligonucleotide attachment. Oligonucleotides modified at the 5' end with carboxylic or aldehyde moieties have been covalently attached on hydrazine-derivatized latex beads (Kremsky et al 1987).

Once the primers and primary analyte binding molecules have been immobilized on the solid support at the appropriate density, a sample containing at least one analyte has been contacted with the primary analyte binding molecule, and a secondary analyte binding molecule as described above has been contacted with at least one analyte, nucleic acid colonies can then be generated by carrying out an appropriate number of cycles of amplification on the nucleic acid template so that each colony comprises multiple copies of the original nucleic acid template and its complementary sequence. One cycle of amplification consists of the steps of hybridization, extension and denaturation and these steps are generally performed using reagents and conditions well known in the art for polymerase chain reaction (PCR).

Examples of nucleic acid polymerases which can be used with the embodiments disclosed herein are DNA polymerase (Klenow fragment, T4 DNA polymerase), heat-stable DNA polymerases from a variety of thermostable bacteria (such as Taq, VENT, Pfu, Tfl DNA polymerases) as well as their genetically modified derivatives (TaqGold, VENTexo, Pfu exo). A combination of RNA polymerase and reverse transcriptase can also be used to generate the amplification of a DNA colony. Preferably the nucleic acid polymerase used for primer extension is stable under PCR reaction conditions, i.e. repeated cycles of heating and cooling, and is stable at the denaturation temperature used, usually approximately 94° C. Preferably the DNA polymerase used is Taq DNA polymerase.

A typical amplification reaction comprises subjecting the solid support and nucleic acid template and primers to conditions which induce primer hybridization, for example subjecting them to a temperature of around 65° C. Under these conditions the oligonucleotide sequence at the 3' end of the nucleic acid template will hybridize to the immobilized primer and in the presence of conditions and reagents to support primer extension, for example a temperature of around 72° C., the presence of a nucleic acid polymerase, for example, a DNA dependent DNA polymerase or a reverse transcriptase molecule (i.e. an RNA dependent DNA polymerase), or an RNA polymerase, plus a supply of nucleoside triphosphate molecules or any other nucleotide precursors, for example modified nucleoside triphosphate molecules, the primer will be extended by the addition of nucleotides complementary to the nucleic acid template sequence.

Nucleic acids which may be amplified according to the methods disclosed herein include DNA, for example genomic DNA, cDNA, recombinant DNA or any form of synthetic or modified DNA, RNA, mRNA or any form of synthetic or modified RNA. Said nucleic acids may vary in length and may be fragments or smaller parts of the larger nucleic acid molecules. Preferably the nucleic acid to be amplified is at least 50 base pairs in length and more preferably 150-400 base pairs in length. The nucleic acid to be amplified may be derived from any source.

A nucleic acid colony can be a discrete area comprising multiple copies of a nucleic acid strand. Multiple copies of the complementary strand to the nucleic acid may also be present in the same colony. The multiple copies of the nucleic acid strands making up the colonies are generally immobilized on a solid support and may be in single or double stranded form. The nucleic acid colonies disclosed herein can be generated in different sizes and densities depending on the conditions used. The size of the colonies is preferably from 0.2 µm to 6 µm, more preferably from 0.3 µm to 4 µm. The density of nucleic colonies for use in the method disclosed herein is typically 10,000/mm$^2$ to 100,000/mm$^2$. It is believed that higher densities, for example, 1,000,000/mm$^2$ to 1,000,000/mm$^2$ and 1,000,000/mm$^2$ to 10,000,000 mm$^2$ may be achieved.

In accordance with various embodiments, one or more nucleic acid colonies can be generated. A nucleic acid colony may be generated from a single immobilized nucleic acid template. In another aspect, a number of nucleic acid colonies are simultaneously produced, each of which may contain different immobilized nucleic acid strands.

In accordance with various embodiments, the nucleoside triphosphate molecules used can be deoxyribonucleotide triphosphates, for example DATP, dTTP, dCTP, dGTP, or are ribonucleoside triphosphates for example dATP, dUTP, dCTP, dGTP. The nucleoside triphosphate molecules may be naturally or non-naturally occurring.

After the hybridization and extension steps, on subjecting the support and attached nucleic acids to denaturation conditions two immobilized nucleic acids will be present, the first being the initial nucleic acid template conjugated to the secondary analyte binding protein and the second being a nucleic acid complementary thereto, extending from one of the immobilized primers. Both the original nucleic acid template conjugated to the secondary analyte binding molecule and the immobilized extended primer formed are then able to initiate further rounds of amplification on subjecting the support to further cycles of hybridization, extension and denaturation. Such further rounds of amplification will result in a nucleic acid colony comprising multiple immobilized copies of the template nucleic acid and its complementary sequence.

The initial immobilization of the template nucleic acid means that the template nucleic acid generally will hybridize with primers located at a distance within the total length of the template nucleic acid. Thus the boundary of the nucleic acid colony formed may be limited to a relatively local area to the area in which the initial template nucleic acid was immobilized. Clearly, once more copies of the template molecule and its complement have been synthesized by carrying out further rounds of amplification, i.e. further rounds of hybridization, extension and denaturation, then the boundary of the nucleic acid colony being generated can extend further, although the boundary of the colony formed may be still limited to a relatively local area to the area in which the initial nucleic acid template was immobilized.

Only one primer and one template nucleic acid are shown in FIG. 1 for simplicity. However, in practice a plurality of primers will be present with a plurality of nucleic acid templates bound to analyte complexes. The plurality of primers may comprise two different primers. However, for simplicity the schematic representation shown in Figure. 1 shows only one type of primer. The plurality of nucleic acid templates may comprise different nucleic acid sequences in the central portion between the oligonucleotides at the 5' and 3' ends respectively. Only one species of nucleic acid template is shown for simplicity in FIG. 1.

The support and the nucleic acid template and immobilized primers are then subjected to conditions which induce primer hybridization. FIG. 1b shows a nucleic acid template that has hybridized to a primer. Such hybridization is enabled by virtue of the fact that the oligonucleotide sequence at the 3' end of the nucleic acid template can hybridize to the primer. In the schematic representation the 3' end oligonucleotide sequence is shown to be complementary to the primer, although in practice an exact complementary sequence is not essential, providing hybridization can occur under the conditions the nucleic acid templates and primers are subjected to.

Here, under appropriate conditions of temperature and in the presence of a DNA polymerase and a supply of nucleotide precursors, for example DATP, dTTP, dCTP and dGTP, the DNA polymerase extends the primer from its 3' end using the nucleic acid template as a template. When primer extension is complete, see FIG. 1c, it can be seen that a second immobilized nucleic acid strand has been generated which is complementary to the initial nucleic acid template. On separating the two nucleic acid strands by, for example heating, two immobilized nucleic acids will be present, the first being the initial nucleic acid template and the second being a nucleic acid complementary thereto, extending from one of the immobilized primers. See FIG. 1c.

Both the original nucleic acid template and the immobilized extended primer formed are then able to hybridize to other primers present (depicted as FIG. 1c) and after a further round of primer extension and strand separation, four single stranded immobilized strands are provided. Two of these contain sequences corresponding to the original nucleic acid template and two contain sequences complementary thereto.

Further rounds of amplification beyond those shown in FIG. 1e can be carried out to result in a nucleic acid colony comprising multiple immobilized copies of the template nucleic acid and its complementary sequence.

In accordance with various embodiments, specific analytes are identified and/or the amount of specific analytes in a sample is measured by the relative presence of nucleic acid colonies amplified. In various embodiments, the amount (or identification) of analyte in a sample is determined by the geospatial location of the nucleic acid colonies (e.g., unique to specific analytes) on the solid support. These nucleic acid colonies can be attached to a solid support as described above. Any method known in the art to detect nucleic acid sequences may be used to detect the nucleic acid colonies generated from the methods described above. Such methods include any sort of visualization or sequencing methods. Such methods include but are not limited to Next Generation Sequencing techniques. Such techniques could be flourophore based or proton based. In various embodiments nucleic acid colonies may be detected using the fluorescent based methods of MISEQ, HISEQ or NEXTSEQ Systems of Illumina. In other various embodiments nucleic acid colonies may be detected using the proton based methods provided by the Ion Torrent based system.

Therefore, in accordance with various methods, where multiple analytes are provided, and multiple corresponding nucleic acid colonies are formed via amplification reactions, specific nucleic acid colonies can be distinguished from other colonies, discretely identifying each nucleic acid colony and, by extension, its corresponding analyte. This can occur regardless of what solid support is provided, whether it be discrete nucleic acid colonies formed adjacent to a specific immobilized primary analyte binding molecules on a flat support such as a slide, flow cell, etc., or whether it be discrete colonies formed on individual beads, where each bead contains a specific immobilized primary analyte binding molecule. Due to, for example, (1) the specific association between primary analyte binding molecule, specific analyte and secondary analyte binding molecule, (2) the specific association between nucleic acid template and analyte via the secondary analyte binding molecule, (3) and the specific association between the nucleic acid template and the nucleic acid colony formed from amplification of the template, each nucleic acid colony can serve as an identifier for a specific analyte. Such associations advantageously allow for identification of specific analyte and determination of amount of specific analyte, particularly in multiplex where signal representative of each analyte is now detectable, as opposed known techniques where multiplex assays are limited based on limited availability of useable fluorophores due to spectral overlap.

II. Kits

In various embodiments, a kit for measuring the amount of analyte in a sample comprising (1) at least one primary analyte binding molecule configured to be immobilized on a solid support; (2) at least one primer configured to be immobilized on the solid support adjacent to the at least one primary analyte binding molecules; and (3) at least one secondary analyte binding molecule; wherein the 5' end of at least one nucleic acid template is conjugated to the at least one secondary analyte binding molecule; and wherein the at least one nucleic acid template comprises an oligonucleotide sequence at the 3' end that hybridizes to the at least one primer, is disclosed.

In some embodiments, a kit for measuring the amount of analyte in a sample comprises (a) at least one primary analyte binding molecule; (b) at least one primer; and (c) at least one secondary analyte binding molecule; wherein the 5' end of at least one nucleic acid template is conjugated to the at least one secondary analyte binding molecule; wherein the at least one nucleic acid template comprises an oligonucleotide sequence at the 3' end that hybridizes to the at least one primer.

Primary analyte binding molecules, their methods of use and manufacture are described in detail above. Briefly, primary analyte binding molecules can be able to bind to a particular analyte with a high degree of affinity and specificity. These primary analyte binding molecules may also be able to be immobilized on a solid support in such a way that it does not disturb the molecules affinity and specificity for a specific analyte molecule. Primary analyte binding molecules may be of any type or composition so long as they are specific and have affinity for a particular analyte. Examples of primary analyte binding molecules include antibodies, antibody fragments, Fab fragments, Fab' fragments, F(ab')2 fragments, scFv proteins, analyte specific trapping agents, nanoparticles, lectins or receptors.

Secondary analyte binding molecules, their methods of use, and manufacture are also described in detail above. Similar to primary analyte binding molecules, secondary analyte binding molecules can be able to bind to a particular analyte with a high degree of affinity and specificity. However, the secondary analyte binding molecules can be conjugated to a nucleic acid template sequence instead of being immobilized on a solid support. Such conjugation may be performed in such a way that preserves the secondary analyte binding molecules' affinity and specificity for a particular analyte.

The nucleic acid template, which is conjugated to the secondary analyte binding molecule, may comprise small oligonucleotide sequences at its 5' and 3' end of the nucleic acid template sequence. The 3' end of the nucleic acid template sequence may be capable of hybridizing with the immobilized primer as described above, and the 5' sequence may be identical to the primer sequence. The kit may also include a filler sequence that is connected to the secondary antibody on one end and connected to the 5' end of the nucleic acid template. In various embodiments the filler sequence is either single stranded or double stranded.

The nucleic acid template may be modified to prevent enzymatic digestion. Examples of said modifications include modifications to the phosphodiester backbone; modifications to the sugar ring; 3' capping with inverted thymidine; and modifications on the nucleotide bases.

The primers for use in this kit have been described in detail above. Briefly, the primers may at their 5' end comprise a means for immobilizing said primer on a solid support. The primers do not need to be unique to each nucleic acid template sequence. Rather, the same one or two primer sequences can be used to amplify the nucleic acid template conjugated to any secondary analyte binding molecule bound to an analyte.

The primers may be modified to prevent enzymatic digestion. Examples of said modifications include modifications to phosphodiester backbone; modifications to the sugar ring; 3' capping with inverted thymidine; and modifications on the nucleotide bases.

In some aspects, the kit might further comprise the solid support. Thus, a further aspect provides a solid support, to which there is attached a plurality of primers as described above and at least one primary analyte binding molecule as described above. Preferably a plurality of primary analyte binding molecules is attached to said solid support. Preferably the attachment of the primary analyte binding molecules and the primers to the solid support is covalent. By performing one or more rounds of nucleic acid amplification on the nucleic acid template(s) bound to the analyte complex using methods as described above, nucleic acid colonies may be formed. A yet further aspect is, therefore, a support comprising one or more primary analyte binding molecules and one or more primers.

In some aspects, the kit might further comprise a solid support where the solid support is a flow cell. In some aspects, the kit might further comprise a solid support wherein the solid support has at least one peak region and one valley region. In various embodiments, the primary analyte binding molecule is bound to the valley region of the solid support. In various embodiments, the kit might provide a primer that is bound at a higher position than said primary analyte binding molecule on the flow cell. In various aspects, the solid support is a bead.

III. Systems

In accordance with various embodiments, a system for measuring the amount of analyte in a sample is provided. A representative system is provided in the schematic diagram of FIG. 10, which illustrates an exemplary system for implementing the methods in accordance with various methods herein.

Figure 10:
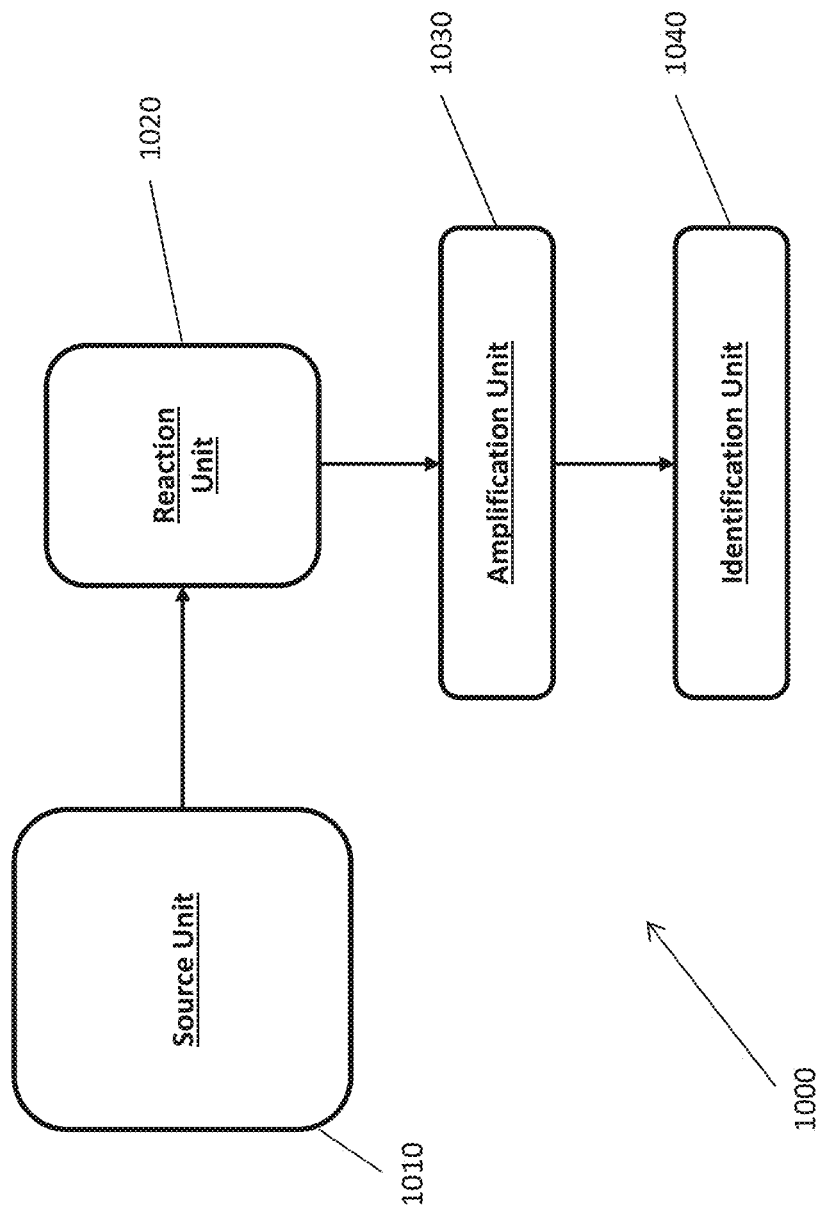
FIG. 10 schematically depicts a system for measuring the amount of analyte in a sample in accordance with various embodiments.

It should be noted that FIG. 10 illustrates one configuration of a system. The orientation and configuration of these components can vary as needed. Moreover, additional components can be added to this system (e.g., a sequencing unit, a display unit) as needed. These various components, their various operations, their various orientations, and various associations between each other will be discussed in detail below.

System 1000 of FIG. 10 can include a source unit 1010. Source unit 1010 can be configured to house a sample comprising a least one analyte, the sample configured to contact at least one primary analyte binding molecule. Source unit 1010 can further be configured to house at least one secondary analyte binding molecule, wherein the 5' end of at least one nucleic acid template is conjugated to the at least one secondary analyte binding molecule, and wherein the at least one nucleic acid template comprises an oligonucleotide sequence at the 3' end.

System 1000 of FIG. 10 can also include a reaction unit 1020. Reaction unit 1020 can be configured to receive a solid support. The solid support can be configured to include at least one primer immobilized on the solid support at the primer 5' end. The solid support can be further configured to include the at least one primary analyte binding molecule immobilized on the solid support, wherein the at least one primer is immobilized adjacent to the at least one primary analyte binding molecule.

Reaction unit 1020 can further be configured to receive the sample comprising the at least one analyte from the source unit, the at least one analyte configured to bind to the at least one primary analyte binding molecule.

Reaction unit 1020 can further be configured to receive the at least one secondary analyte binding molecule from the source unit, the at least one secondary analyte binding molecule configured to bind to the at least one analyte, wherein the oligonucleotide sequence at the 3' end of the nucleic acid template hybridizes to the primer.

The solid support, configured to be received in reaction unit 1020, can be a flow cell. The flow cell can have at least one peak region and one valley region. The primary analyte binding molecule can be bound to the valley region. The at least one primer can be bound at a higher position than said primary analyte binding molecule on the flow cell. Alternatively, the at least one primer can be bound to the peak region.

In another aspect, the solid support can be a bead.

System 1000 of FIG. 10 can also include an amplification unit 1030. Amplification unit 1030 can be configured to perform one or more nucleic acid amplification reactions on the at least one nucleic acid template, so that nucleic acid colonies are generated.

System 1000 of FIG. 10 can also include an identification unit 1040 configured to identify the specific nucleic acid colony associated with the specific analyte to determine the amount of analyte in a sample. The amount of analyte in a sample can be determined by the presence of the nucleic acid colonies in a specific region of the flow cell. Further, the identification unit can be configured to identify each specific nucleic acid colony from a plurality of nucleic acid colonies, each nucleic acid colony associated with a specific analyte, to determine the amount of each analyte present. As such, where multiple analytes are provided to the system, and multiple corresponding nucleic acid colonies are formed via the amplification unit, identification unit 1040 can distinguish one nucleic acid colony from another, discretely identifying each nucleic acid colony and, by extension, its corresponding analyte. This can occur regardless of what solid support is provided, whether it be discrete nucleic acid colonies formed adjacent to a specific immobilized primary analyte binding molecules on a flat support such as a slide, flow cell, etc., or whether it be discrete colonies formed on individual beads, where each bead contains a specific immobilized primary analyte binding molecule. Due to, for example, (1) the specific association between primary analyte binding molecule, specific analyte and secondary analyte binding molecule, (2) the specific association between nucleic acid template and analyte via the secondary analyte binding molecule, (3) and the specific association between the nucleic acid template and the nucleic acid colony formed from amplification of the template, each nucleic acid colony can serve as an identifier for a specific analyte. Such associations advantageously allow for identification of specific analyte and determination of amount of specific analyte, particularly in multiplex.

Identification unit 1040 can further comprise a sequencing unit that is configured to determine the presence of the nucleic acid colonies using DNA sequencing.

As it relates to orientation, each component (e.g., unit) depicted can be implemented as integrated with another system component as needed. By integrated, any one component can be in communication with another component such as, for example, by physical proximity, physical connection, data communication, fluid communication, and so on. That is, source unit 1010 and reaction unit 1020 can be housed in the same housing assembly and communicate via conventional device/component connection means (e.g. serial bus, optical cabling, electrical cabling, etc.). Similarly, for example, reaction unit 1020 and amplification unit 1030 can be housed in the same housing assembly and communicate via conventional device/component connection means (e.g. serial bus, optical cabling, electrical cabling, etc.). Moreover, all components can be provided as part of a single integrated instrument system assembly, as opposed to discrete components independently housed.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In some embodiments, the system for measuring the amount of analyte in a sample comprises (a) a source unit configured to house a sample comprising a least one analyte, the sample configured to contact at least one primary analyte binding molecule, and at least one secondary analyte binding molecule, wherein the 5' end of at least one nucleic acid template is conjugated to the at least one secondary analyte binding molecule, and wherein the at least one nucleic acid template comprises an oligonucleotide sequence at the 3' end; (b) a reaction unit configured to receive (1) at least one primer and (2) the at least one primary analyte binding molecule; the sample comprising the at least one analyte from the source unit, the at least one analyte configured to bind to the at least one primary analyte binding molecule, and the at least one secondary analyte binding molecule from the source unit, the at least one secondary analyte binding molecule configured to bind to the at least one analyte, wherein the oligonucleotide sequence at the 3' end of the nucleic acid template hybridizes to the primer; (c) an amplification unit configured to perform one or more nucleic acid amplification reactions on the at least one nucleic acid template, so that a nucleic acid colony is generated; and (d) an identification unit configured to identify the specific nucleic acid colony associated with the specific analyte to determine the amount of analyte in a sample.

IV. Example

Oligos were designed to have a 20-30 bp sequence at the '3 end and 5' end of the full-length oligo and a unique region random sequence (URRS), which was designed to minimize secondary structure and amplification by primer sequences. The oligo was conjugated to a secondary antibody by reacting antibody against IL-2 at a concentration of 0.5-2.5 mg/ml (20-300 µg in 20-300 µl of the buffer) in PBS (pH range 5-9) without BSA or azide; and oligo at a concentration of 20-300 µM (20-300 µl total volume of oligo) in PBS (pH range 5-9) without TRIS.

Figure 12:
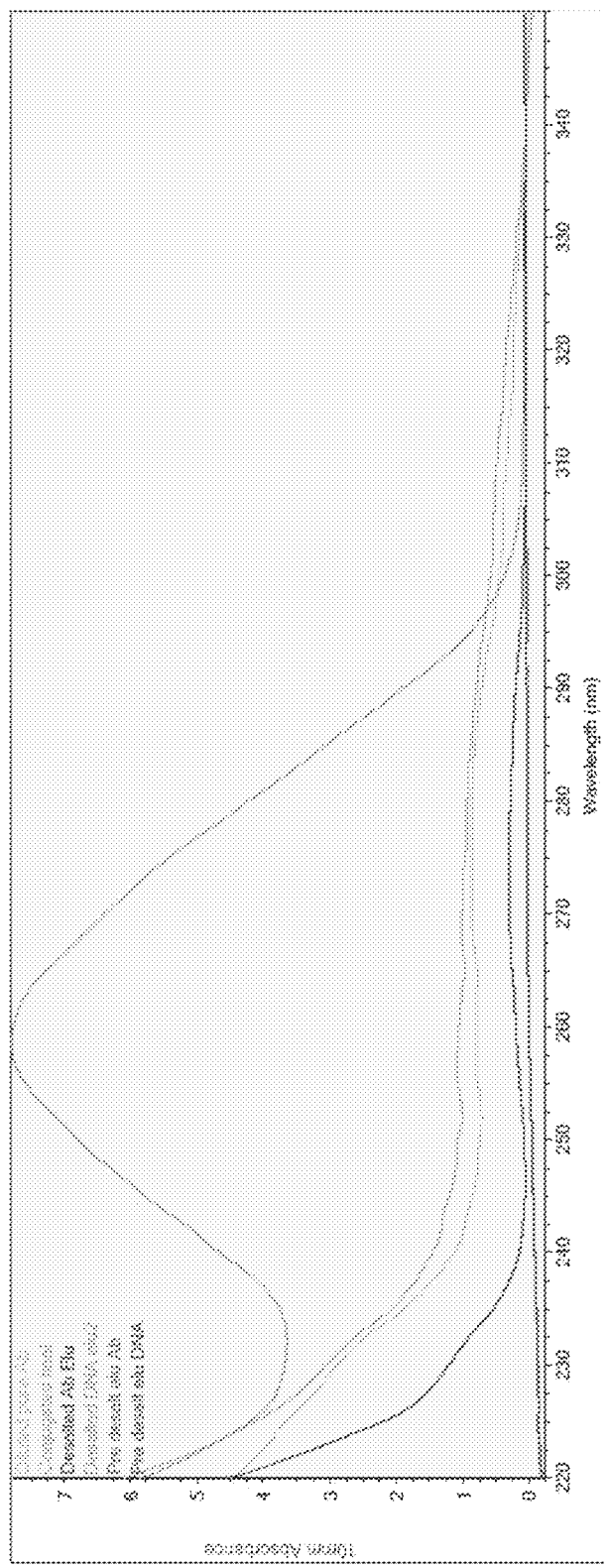
FIG. 12 is a graph showing absorbance data for an example of an antibody-oligo conjugate in accordance with various embodiments.
Figure 13:
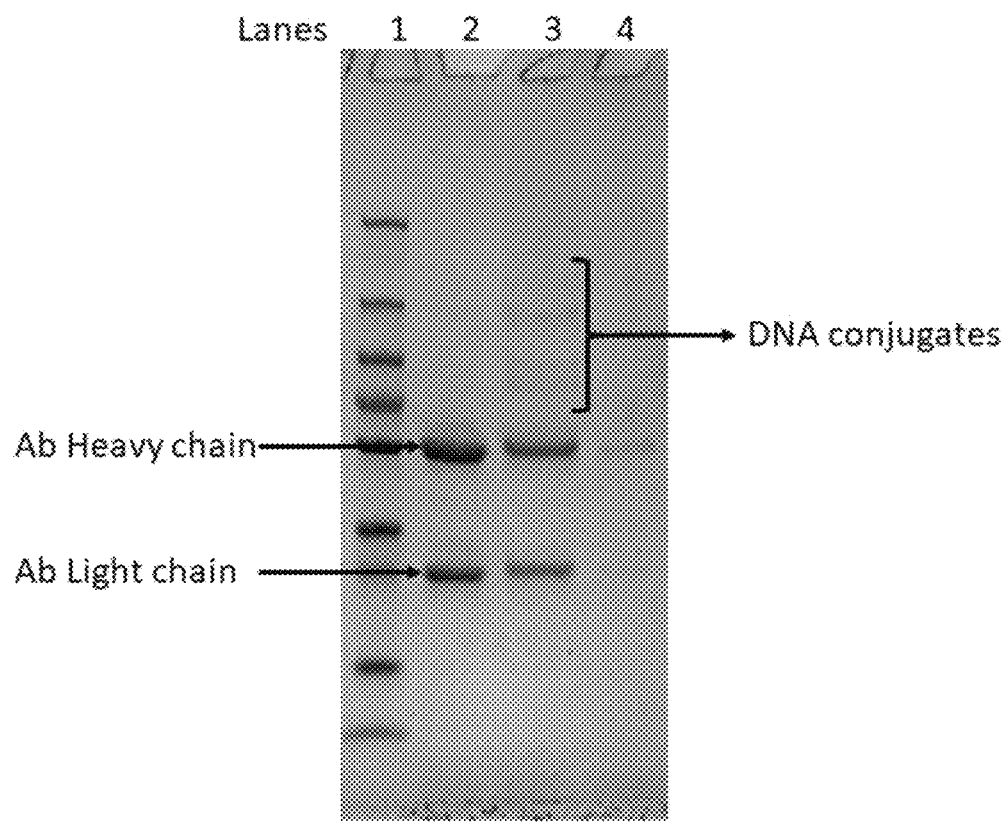
FIG. 13 is a picture of a gel showing antibody before and after conjugation with oligo in accordance with various embodiments.

After conjugation, the antibody-oligo conjugates were purified using centrifugation. Absorbance of the oligo, antibody, and antibody-oligo conjugate were measured (FIG. 12 and Table 1). Samples of the antibody and the antibody-oligo conjugate were analyzed by gel electrophoresis (FIG. 13).

TABLE 1

Absorbance of oligo, antibody, and antibody-oligo conjugate.

| # | Sample ID | User name | Protein Conc. | Unit | A280 | 260/280 | Sample Type |
|---|---|---|---|---|---|---|---|
| 2 | Pre desalt elu DNA | Nanodrop User | −0.033 | mg/ml | −0.033 | 1.87 | 1 Abs = 1 mg/mL |
| 3 | Pre desalt elu Ab | Nanodrop User | −0.033 | mg/ml | −0.033 | 1.87 | 1 Abs = 1 mg/mL |
| 5 | Desalted DNA elu2 | Nanodrop User | 4.193 | mg/ml | 4.193 | 1.84 | 1 Abs = 1 mg/mL |
| 7 | Desalted Ab Elu | Nanodrop User | 0.224 | mg/ml | 0.224 | 0.64 | 1 Abs = 1 mg/mL |
| 8 | Conjugated final* | Nanodrop User | 0.877 | mg/ml | 0.877 | 1.14 | 1 Abs = 1 mg/mL |
| 9 | Diluted pure Ab** | Nanodrop User | 0.807 | mg/ml | 0.807 | 0.91 | 1 Abs = 1 mg/mL |

The activity of the conjugated antibody was measured using competition ELISA. The assay was performed on the capture ELISA format. In brief, antibodies were physically adsorbed on a plastic/glass/silica surface or a polymer bead surface, and analytes were captured on the capture antibody. Next, the oligo-conjugated detection antibody was added. Excess detection antibody was washed off on subsequent wash steps. Then biotinylated secondary antibody to IL-2 was added followed by Avidin-HRP conjugates. After multiple washing steps, high sensitivity TMB-Acid neutralization was used to quantitate the signal. Conjugated antibody retains the ability to bind to IL-2, and therefore displays a lower absorbance value. As shown in table 2, reaction wells comprising DNA-Ab conjugates showed a lower absorbance value than reaction wells comprising no DNA-Ab conjugates.

TABLE 2

Absorbance of the TMB substrate at 450 nm from competition ELISA between DNA conjugated Ab and the Biotinylated antibody

| IL-2 conc. (pg/ml) | Amount of DNA-Ab conjugates (µl/ml) | Absorbance of TMB substrate at 450 nm |
|---|---|---|
| 15.6 | 0.125 | 0.069 |
| 15.6 | 0.25 | 0.0635 |
| 15.6 | 0.5 | 0.063 |
| 15.6 | 1 | 0.0585 |
| 15.6 | 0 | 0.0995 |

To quantitate IL-2 in the sample using conjugated antibody, capture ELISA was performed. In brief, primary capture antibodies were physically adsorbed on a plastic/glass/silica surface or a polymer bead surface, and analytes were captured on the capture antibody. Next, the detection oligo-conjugated detection antibody was added. Excess detection antibody was washed off on subsequent wash steps. The oligo-Ab complexes were eluted using either low pH buffer or high salt containing buffer, digestion with sequence specific endonucleases or incubation at 95° C. for 10 minutes either used individually or in combination.

After running the assay, qPCR using universal primers and next generation sequencing were used to confirm the presence of the oligo attached to the antibody, which confirmed the presence of the target analyte. Eluted oligo samples were either PCR amplified and/or diluted. After sequencing, output sequences were decoded for each analyte and the standard curve for each specific analyte was prepared. Quantitation of multiple analytes was performed by computational methods that generated a summary of the experiment, standard curves for each analyte, QC parameters, and a table of the quantitation of each analyte for a given sample.

Taken together, these results demonstrate that a detection oligo can be conjugated to an antibody, and used for detection of an analyte.

What is claimed:

1. A method of measuring the amount of analyte in a sample comprising the steps of:

a) contacting a sample comprising at least one analyte with at least one primary analyte binding molecule; wherein the at least one primary analyte binding molecule is immobilized on a solid support; wherein the analyte binds to the at least one primary analyte binding molecule;
b) contacting at least one secondary analyte binding molecule with the at least one analyte,
wherein the 5' end of at least one nucleic acid template is conjugated to the at least one secondary analyte binding molecule; and
wherein the at least one nucleic acid template comprises an oligonucleotide sequence at the 3' end that hybridizes to a primer; wherein the primer is immobilized at the 5' end on the solid support;
c) hybridizing the oligonucleotide sequence to the primer;
d) performing one or more nucleic acid amplification reactions on the at least one nucleic acid template, so that nucleic acid colonies are generated; and
e) measuring the presence of the nucleic acid colonies to determine the amount of the specified analyte in a sample,
wherein the solid support is a flow cell with at least one peak region and one valley region, wherein the primary analyte binding molecule is bound to the valley region of the flow cell, and wherein the primer is bound at a higher position than said primary analyte binding molecule on the flow cell.

2. The method of claim 1, wherein the primary analyte binding molecule is selected from the group consisting of: antibodies, antibody fragments, Fab fragments, Fab' fragments, F(ab')2 fragments, scFv proteins, analyte specific trapping agents, and nanoparticles.

3. The method of claim 1, wherein the secondary analyte binding molecule is selected from the group consisting of: antibodies, antibody fragments, Fab fragments, Fab' fragments, F(ab')2 fragments, scFv proteins, analyte specific trapping agents, and nanoparticles.

4. The method of claim 1, wherein the primer is modified to reduce enzymatic digestion.

5. The method of claim 4, wherein the modification is selected from the group consisting of: modifications of the phosphodiester backbone; modifications to the sugar ring; 3' capping with inverted thymidine; and modifications on the nucleotide bases.

6. The method of claim 1, wherein the nucleic acid template sequence is modified to reduce enzymatic digestion.

7. The method of claim 6, wherein the modification is selected from the group consisting of: modifications of the phosphodiester backbone; modifications to the sugar ring; 3' capping with inverted thymidine; and modifications on the nucleotide bases.

8. The method of claim 1, wherein the nucleic acid sequence template at its 5' end further comprises an oligonucleotide sequence that is identical to the primer sequence.

9. The method of claim 1, wherein the nucleic acid template sequence is the reverse mirror image of its complementary sequence.

10. The method of claim 1, wherein the 5' end of a filler is attached to the secondary analyte binding molecule and the 3' end of said filler is attached to the 5' end of the nucleic acid template sequence.

11. The method of claim 10, wherein said filler sequence is double-stranded.

12. The method of claim 1, wherein the amount of analyte in a sample is determined by the presence of a unique recognition sequence associated with a particular analyte binding molecule.

13. The method of claim 1, wherein the amount of analyte in a sample is determined by the presence of the nucleic acid colonies in a specific region of the flow cell.

14. The method of claim 1, where the presence of the nucleic acid colonies is measured using DNA sequencing methods.

* * * * *